United States Patent [19]

Fisher et al.

[11] Patent Number: 5,998,597
[45] Date of Patent: *Dec. 7, 1999

[54] METHOD FOR IMPROVED SELECTIVITY IN PHOTO-ACTIVATION OF MOLECULAR AGENTS

[75] Inventors: Walter G. Fisher, Knoxville; Eric A. Wachter, Oak Ridge; H. Craig Dees, Knoxville, all of Tenn.

[73] Assignee: Photogen, Inc., Knoxville, Tenn.

[*] Notice: This patent is subject to a terminal disclaimer.

[21] Appl. No.: 08/989,231

[22] Filed: Dec. 11, 1997

Related U.S. Application Data

[62] Division of application No. 08/739,801, Oct. 30, 1996.

[51] Int. Cl.⁶ .............................. C07H 21/64; C07K 5/00; C07K 14/00; A61B 19/00
[52] U.S. Cl. .................. 536/23.1; 536/23.1; 530/300; 530/350; 514/44; 600/300; 600/476; 607/89; 607/99; 607/2; 607/3; 128/898
[58] Field of Search .............................. 514/44; 600/300, 600/476; 435/6, 91.1, 91.31, 440, 375; 530/350, 300; 536/23.1; 128/898

[56] References Cited

U.S. PATENT DOCUMENTS

| | | | |
|---|---|---|---|
| 4,578,079 | 3/1986 | Ruoslahti et al. | 435/197 |
| 4,589,881 | 5/1986 | Pierschbacher et al. | 623/11 |
| 4,822,335 | 4/1989 | Kawai et al. | 604/20 |
| 4,925,736 | 5/1990 | Shikowitz | 424/449 |
| 4,973,848 | 11/1990 | Kolobanov et al. | 250/458.1 |
| 5,034,613 | 7/1991 | Denk et al. | 250/458.1 |
| 5,053,006 | 10/1991 | Watson | 604/52 |
| 5,231,984 | 8/1993 | Santana-Blank | 128/395 |
| 5,498,694 | 3/1996 | Ruoslahti | 530/324 |
| 5,558,666 | 9/1996 | Dewey et al. | 606/9 |
| 5,576,013 | 11/1996 | Williams et al. | 424/423 |
| 5,586,981 | 12/1996 | Hu | 606/9 |
| 5,622,699 | 4/1997 | Ruoslahti et al. | 424/93.6 |
| 5,627,263 | 5/1997 | Ruoslahti et al. | 530/327 |
| 5,629,291 | 5/1997 | Ruoslahti et al. | . |
| 5,643,334 | 7/1997 | Eckhouse et al. | 620/20 |
| 5,654,267 | 8/1997 | Vuori et al. | 514/2 |
| 5,832,931 | 11/1998 | Fisher et al. | 128/898 |

OTHER PUBLICATIONS

J.W. Tessman, et al., "Photochemistry of Furan–Side 8–Methoxypsoralen–Tymidine Monoadduct Inside the DNA Helix, Conversion to Diadduct and to Pyrone–Side Monoadduct," Biochemistry, 24 *1985) 1669–1676.

J.C. Kennedy, et al., "Photodynamic Therapy with Endogenous Protoporphyrin IX: Basic Principles and Present Clinical Experience," J. of Photochemistry and Photobiology, B: Biology, 6 (1990) 143–148.

K. Teuchner, et al., "Spectroscopic Properties of Potential Sensitizers for New Photodynamic Therapy Start Mechanisms via Two–Step Excited Electronic States," Photochemistry and Photobiology 57 (1993) 465–471.

A.R. Young, "Photocarcinogenicity of Psoralens Used in PUVA Treatment: Present Status in Mouse and Man," J. of Photochemistry and Photobiology, B: Biology, 6 (1990) 237–247.

M.J. Wirth, et al., "Two–Photon Excited Molecular Fluorescence in Optically Dense Media," Analytical Chemistry, 49 (1977) 2054–2057.

M.J. Sepaniak, et al., "Laser Two–Photon Excited Molecular Fluorescence Detection for High Pressure Liquid Chromatography," Analytical Chemistry, 49 (1977) 1554–1556.

M.J. Sepaniak, et al., "High–Performance Liquid Chromatographic Studies of Coal Liquids by Laser–Based Detectors," J. Of Chromatography, 211 (1981) 95–102.

W.D. Pfeffer, et al., "Laser Two–Photon Excited Fluorescence Detector for Microbore Liquid Chromatography," Analytical Chemistry, 58 (1986) 2103–2105.

M.J. Wirth, et al., "Very High Detectability in Two–Photon Spectroscopy," Analytical Chemistry, 62 (1990) 2103–2105.

J.E. Hearst, et al., "The Reaction of the Psoralens with Deoxyribonucleic Acid", Quarterly Review of Biophysics, 17 (1984) 1–44.

Pierce, Jr. et al., "Conspectus" Comprehensive Therapy 16(4):3–8.

Amato "Hope for a Magic Bullet that Moves at the Speed of Light" Science 262:32–33.

Schmidt–Erfurth et al., "Photodynamic Therapy of Experimental Choroidal Melanoma Using Lipoprotein–delivered Benzoporphyrin" Opthalmology 101:89–99.

Rosenthal et al., "Clinical Application of Photodynamic Therapy" Ann Med. 26:405–9.

Marcus et al., "Photodynamic Therapy for the Treatment of Squamous Cell Carcinoma Using Benzoporphyrin Derivative" J. Dermatol Sung Oncol 20:375–382.

Kung–Turg et al., "Therapeutic Effects of Photosensitizer in Combination with Laser and ACNO on an in Vivo or in Vitro Model of Celebral Glioma" Chinese Medical Journal 108(2):98–104.

(List continued on next page.)

*Primary Examiner*—Nancy Degen
*Assistant Examiner*—Janet Epps
*Attorney, Agent, or Firm*—Cook, Alex, McFarron, Manzo, Cummings & Mehler, Ltd.

[57] ABSTRACT

A method for the treatment of a particular volume of plant or animal tissue comprising the steps of treating the plant or animal tissue with at least one photo-active molecular agent, wherein the particular volume of the plant or animal tissue retains at least a portion of the at least one photo-active molecular agent, and then treating the particular volume of the plant or animal tissue with light sufficient to promote a simultaneous two-photon excitation of at least one of the at least one photo-active molecular agent retained in the particular volume of the plant or animal tissue, wherein the at least one photo-active molecular agent becomes active in the particular volume of the plant or animal tissue. There is also disclosed a method for the treatment of cancer in plant or animal tissue and a method for producing at least one photo-activated molecular agent in a particular volume of a material.

23 Claims, 22 Drawing Sheets

OTHER PUBLICATIONS

Castro, et al., "The Concept of Laser Phototherapy" Laser Applications in Otolaryngology 29(b):1011–29.

Fisher, A.M.R. et al. "Clinical and Preclinical Photodynamic Therapy" Laser Surg. Med. 1 7, 2–31 (1995).

Cheong, W–F. et al., "A Review of the Optical Properties of Biological Tissues" IEEE 5. Quant. Election 2 6, 2166–2185 (1990).

Dougherty, T.J. et al., "Photoradiation Therapy II Cure of Animal Tumors With Hematoporphyrin and Light" J. Nat'l Cancer–Inst. 5 5, 115–120 (1975).

Gomer, C.J. et al. (1989) Properties and applications of photodynamic therapy. Rad. Res. 1 2 0, 1–18.

Kessel, D. et al., (1991) Photophysical and photobiological properties of diporphyrin ethers. Photochem. Photobiol. 5 3,469–474.

Dolphin, D., (1994) 1993 Syntex award lecture, photomedicine and photodynamic therapy. Can. J. Chem. 7 2, 1005–1013.

Katsumi, T.A., et al., (1996) Photodynamic therapy with a diode laser for implanted fibrosarcoma in mice Employing mono–L–aspartyl chlorin E6. Photochem. Photobiol. 6 4, 671–675.

Göpert–Mayer, M., (1931) Elementary process with two quantum jumps. Ann. Physik 9, 273–294.

Kaiser, W. and C.G.B. Garrett, (1961) Two photon excitation in $CaF_2:Eu^{2+}$. Phys. Rev. Lett. 7, 229–231.

Monson, P.R. and W.M. McClain (1970) Polarization dependence of the two–photon absorption of tumbling molecules with application of liquid 1–choronaphthalene and benzene. J. Chem. Phys. 5 3, 29–37.

Wilson, B.C. and M.S. Patterson, (1986) The physics of photodynamic therapy. Phys. Med. Biol. 3 1, 327–360.

Draumer, N.H., et al., (1997) Femtosecond dynamics of excited–state evolution in $[Ru(bpy)_3]^{2+}$. Science 2 7 5, 54–57.

Swofford, R.L. and W.M. McClaim, (1975) The effect of saptial and temporal laser beam characteristics on two–photon absorption. Chem. Phys. Lett. 3 4, 455–459.

Hammer, D.X. et al., (1996) Experimental investigation of ultrashort pulse laser–induced breakdown thresholds in aqueous media. Ieee J. Quant. Electron. 3 2, 670–678.

Andreoni, A., et al., (1982) Two–step lazer activation of hematoporphyrin derivative. Chem. Phys. Lett. 8 8, 37–39.

Shea C.R., et al., (1990) Mechanistic investigation of doxycyckine photosensitization by picosecond–pulsed and continuous wave laser irradiation of cells in culture. J. Biol. Chem. 2 6 5, 5977–5982.

Inaba, H., et al., (1985) Nd:YAG laser–induced hematoporphyrin visible flourescence and two–photon–excited photochemical effect on malignant tumor cells. J. Opt. Soc. Am. A:Opt. Inage Science 2, P72 (mtg abstr).

Mashiko, S., et al., (1986) Two–photon excited visible flourescence of hematoporphyrin and phiophorbide a and in vitro experiments of the photodynamic . . . J. Opt. Soc. Am. B:Opt. Phys 3, P72–P73 (mtg. abstr).

Yamashita, Y. et al., (1991) Photodynamic therapy using pheophorbide–a and Q–switched Nd:YAG laser on implanted human hepatocellular carcinoma. Gast. Jap. 2 6, 623–627.

Fugishima, I., et al., (1991) Photodynamic therapy using phophorbide a and ND:YAG laser. Neurol. Med. Chir. (Tokyo) 3 1, 257–263.

Mashiko, S., et al., (1985) Basic study on photochemical effect of pheophorbide–a irradiated by Nd:YAG laser light. Nippon Laser Igakukaishi 6,113–116.

Steil, H., et al., (1993) Photophysical properties of the photosensitizer phophorbide a studied at high photon flux densities. J. Photochem. Photobiol. B: Biology 1 7, 181–186.

Bodaness, R.S. and D.S. King (1985) The two–photon induced flourescence of the tumor localizing photo–sensitizer hematoporphyrin derivative via 1064 nm . . . Biochem. Biophys. Res. Comm. 1 2 6, 346–351.

Bodaness, R.S., et al., (1986) Two–photon laser–induced fluorescence of the tumor–localizing photosensitive hematoporphyrin derivative. J. Biol. Chem. 2 6 1, 12098–12101.

Lenz, P., (1995) In vivo excitation of photosensitizers by infrared light. Photochem. Photobiol. 6 2, 333–338.

Patrice, T., et al., (1983) Neodymium–yttrium aluminum garnet laser destruction of nonsensitized and hematoporphyrin derivative–sensitized tumors. Canc. Res. 4 3, 2876–2879.

Song, P.S. and K.J. Tapley, Jr. (1979) Photochemistry and photobiology of psoralens. Photochem. Photobiol. 2 9, 1177–1197.

Cimino, G.D., et al., (1985) Psoralens as photoactive probes of nucleic acid structure and function: organic chemistry, photochemistry, and biochemistry. Ann. Rev. Biochem. 5 4, 1151–1193.

Fisher, W.G., et al., (1997) Two–photon spectroscopy and photochemistry of tris(2,2'–bipyridine)–ruthenium(II). J. Phys. Chem. (in press).

Moscatelli, F.A., (1985) A simple conceptual model for two–photon absorption. Am. J. Phys. 5 4, 52–54.

Fisher, W.G., et al., (1997) The titanium:sapphire laser as an excitation source in two–photon spectroscopy. Appl. Spctrosc. 5 1, (in press).

Lytle, F.E., et al., (1980) Two–photon excitation of polycyclic aromatic hydrocarbons. Intern. J. Environ. Anal. Chem. 8, 303–312.

Peticolas, W.L., (1967) Multiphoton spectroscopy. Ann. Rev. Phys. Chem. 1 8, 233–260.

McClain, W.M., (1974) Two–photon molecular spectroscopy. Acc. Chem. Res. 7, 129–135.

McClain, W.M., (1971) Excited state symmetry assignment through polarized two–photon absorption studies of fluids. J. Chem. Phys. 5 5, 2789–2796.

Hermann, J.P. and J. Ducuing, (1972) Dispersion of the two–photon cross section in rhodamine dyes. Opt. Comm. 6, 101–105.

Niemz, M.H., (1995) Theshold dependence of laser–induced optical breakdown on pulse duration. Appl. Phys. Lett. 6 6, 1181–1183.

Kennedy, S.M. and F.E. Lytle, (1986) p–Bis(o–methylstryl-)benzene as a power–squared sensor for two–photon absorption measurement between 537 and 694 nm. Anal. Chem. 5 8, 2643–2647.

Chan, C.K. and S.O. Sari, (1974) Tunable dye laser pulse converter for production of picosecond pulses. Appl. Phys. Lett. 2 5, 403–406.

Harris, J.M., et al., (1975) Pulse generation in cw–dye laser by mode–locked synchronous pumping. Appl. Phys. Lett. 2 6, 16–18.

Spence, D.E., et al., (1991) 60–fsec pulse generation from a self–mode–locked Ti:Sapphire laser. Opt. Lett. 1 6, 42–44.

Georges, J., et al., (1996) Limitations arising from optical saturation in fluorescence and thermal lens spectrometries using pulsed laser excitation: application to the . . . Appl. Spectrosc. 5 0, 1505–1511.

Marchesini, R., et al., (1986) A study on the possible involvement of nonlinear mechanism of light absorption by HpD with Nd:YAG laser. Lasers Surg. Med. 6, 323–327.

Oh, D.H., et al., (1997) Two–photon excitation of 4'–hydroxymethyl–4,5', 8–trimethylpsoralen. Photochem. Photobiol. 6 5, 91–95.

Prasad, P.N. and G.S. He, (1996) Multiphoton resonant nonlinear–optical processes in organic molecules ACS Symposium Series 6 2 8, 225–236.

Dagani, R., (1996) Two photons shine in 3–D data storage. Chem Eng. News, Sep. 23, 1996, 68–70.

Lytle, F.E., (1981) Laser fundamentals. In Lasers in Chemical Analysis (Ed.: G.M. Hieftje, et al.) 5–6. The Humana Press, New Jersey.

P.M. Johnson, et al. "The Discovery of a 3p Rydberg State in Benzene By Three–Photon Resonant Multiphoton Ionization Spectroscopy" Chemical Physics Letters, pp. 53–56 (1983).

S.G. Grubb, et al. "The three–photon spectrum of the $^1B_{2u}-^1A_{1g}$ transition in benzene: Analysis of vibronic and rotational structure" J. Chem. Phys. 81 (12), American Institute of Physics, pp. 5255–5265 (1984).

J.R. Cable, et al. "A condensed phase study of the benzene $B_{2u}-^1A_{1g}$ three–photon transition" J. Chem. Phys. 85 (6), American Institute of Physics, pp. 3155–3164 (1986).

Philip M. Johnson, "The multiphoton ionization spectrum of trans–1,3 butadiene" Journal of Chem. Physics, vol. 64, No. 11, pp. 4638–4644 (1976).

Mark Seaver, et al. "Double Resonance Multiphoton Ionization Studies of High Rydberg States in NO", J. Phys. Chem, 1983, 87, pp. 2226–2231. American Chemical Society.

E.A. Wachter, Fisher et al. "Titanium: Sapphire Laser as an Excitation Source In Two–Photon Spectroscopy" Applied Spectroscopy, vol. 51, No. 2, pp. 218–226 (1997).

Sun–Yung Chen, et al. "Theory of two–photon induced fluorescence anisotropy decay in membranes" Biophys. J. Biophysical Society, vol. 64, pp. 1567–1575 (May 1993).

Joseph R. Lakowicz, et al. "Two–Color Two–Photon Excitation of Fluorescence" Photochemistry and Photobiology, pp. 632–635 (1996).

George C. Nieman, et al. "A new electronic state of ammonia observed by multiphoton ionization", J. Chem. Phys. 68(12) pp. 5656–5657 (1978).

Philip M. Johnson, "The multiphoton ionization spectrum of benzene" Journal of Chemical Physics, vol. 64, No. 10, 4143–4148 (May 1976).

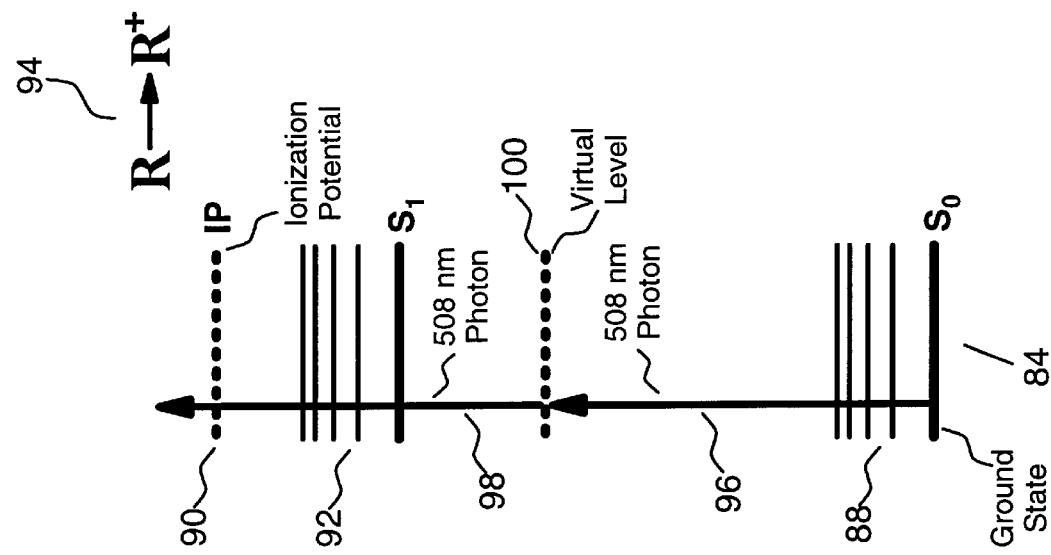
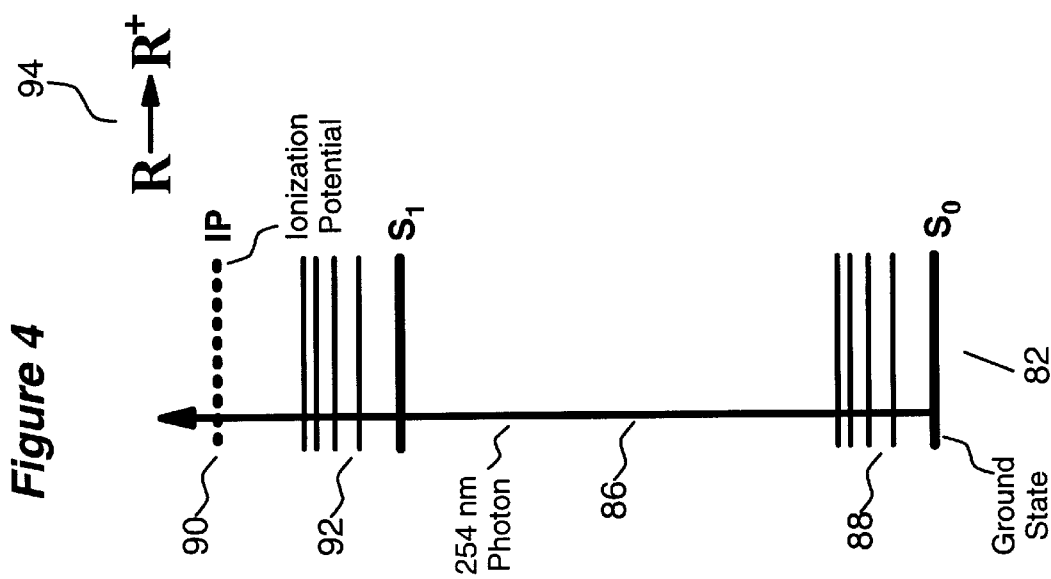
Figure 4

METHOD FOR IMPROVED SELECTIVITY IN PHOTO-ACTIVATION OF MOLECULAR AGENTS

This application is a division of application Ser. No. 08/739,801, filed Oct. 30, 1996, now pending.

This invention was made with Government support under Contract No. DE-AC05-84OR21400 awarded by the U.S. Department of Energy to Lockheed Martin Energy Systems, Inc. Lockheed Martin Energy Systems, Inc., and the Oak Ridge Associated Universities have waived rights to this invention to the inventors. The Government has rights in this invention pursuant to Contract No. DE-AC05-84OR21400 awarded by the U.S. Department of Energy.

FIELD OF THE INVENTION

The present invention relates generally to methods and apparatus for achieving selective photo-activation of one or more molecular agents with a high degree of spatial control. The method taught for achieving selective photo-activation utilizes the special properties of non-linear optical energy for exciting or promoting an agent from one molecular energy level to another with a high degree of spatial and molecular specificity. The special features of this method are applicable in the processing of various types of materials, and in particular afford distinct advantages in the treatment of diseases in humans and animals. Specifically, use of non-linear excitation methods facilitate controlled therapeutic activation of photodynamic therapy agents in deep tissue using near infrared to infrared radiation, which is absorbed and scattered to a lesser extent than methods and radiations currently used.

BACKGROUND OF THE INVENTION

An urgent need exists in many fields for a method that is capable of selectively controlling the activation of various molecular agents. The desired improvements in activation include enhancements in spatial or temporal control over the location and depth of activation, reduction in undesirable activation of other co-located or proximal molecular agents or structures, and increased preference in the activation of desirable molecular agents over that of undesirable molecular agents. Various linear and non-linear photo-chemical and photophysical methods have been developed to provide some such improvements for some such agents. However, in general the performance and applicability of these methods have been less than desired. Specifically, improved photo-activation methods are needed that may be used to selectively photo-activate a variety of molecular therapeutic agents while providing improved performance in the control of application of this photo-activation.

Application of optical radiation for probing or transformation of molecular agents has been known for many years. Linear optical excitation has been extensively studied as a means for achieving semi-selective activation of molecular therapeutic agents. For example, Tessman et al. (J. W. Tessman, S. T. Isaacs and J. E. Hearst, "Photochemistry of the Furan-Side 8-Methoxypsoralen-Thymidine Monoadduct Inside the DNA Helix. Conversion to Diadduct and to Pyrone-Side Monoadduct," Biochemistry, 24 (1985) 1669–1676) teach of the application of light at specific energies as a means for achieving partial selectivity in the formation of molecular bonds between target molecular agents and DNA (deoxyribonucleic acid). Kennedy et al. (J. C. Kennedy, R. H. Pottier and D. C. Ross, "Photodynamic Therapy with Endogenous Protoporphyrin IX: Basic Principles and Present Clinical Experience," Journal of Photochemistry and Photobiology, B: Biology, 6 (1990) 143–148) review progress on development and application of various photosensitive molecular agents for clinical treatment of disease. And Teuchner et al. (K. Teuchner, A. Pfarrherr, H. Stiel, W. Freyer and D. Leupold, "Spectroscopic Properties of Potential Sensitizers for New Photodynamic Therapy Start Mechanisms via Two-Step Excited Electronic States," Photochemistry and Photobiology, 57 (1993) 465–471) teach of the use of spectroscopic properties for selection of candidate photo-active agents. Yet performance of these agents and specifically the methods used for their activation have not been as successful as desired. For example, Young (A. R. Young, "Photocarcinogenicity of Psoralens Used in PUVA Treatment: Present Status in Mouse and Man," Journal of Photochemistry and Photobiology, B: Biology, 6 (1990) 237–247) presents strong evidence that the optical radiation used in common treatment regimes based on linear optical excitation of photosensitive molecular agents can itself produce disease and other undesirable side effects. Furthermore, a less than desirable penetration depth has plagued most efforts at linear optical excitation of molecular therapeutic agents, primarily as a consequence of the effects of optical scatter and of absorbance of the incident probe radiation at wavelengths near the linear absorption bands of these agents. In fact, virtually all examples of the use of linear optical excitation for molecular transformation are plagued by fundamental performance limits that are attributable to undesirable absorption and scatter of the incident optical radiation by the surrounding matrix, poor specificity in excitation of probe molecular species, and a lack of suitable physical mechanisms for precise control of the extent and depth of activation.

Various non-linear optical excitation methods have been employed in an effort to achieve specific improvements in the selectivity of photo-activation for certain applications, and to address many of the limitations posed by linear excitation methods. Excitation sources ranging from single-mode, continuous wave (CW) lasers to pulsed Q-switched lasers having peak powers in excess of 1 GW have been employed with these methods. For example, Wirth and Little (M. J. Wirth and F. E. Lytle, "Two-Photon Excited Molecular Fluorescence in Optically Dense Media," Analytical Chemistry, 49 (1977) 2054–2057) teach use of non-linear optical excitation as a means for stimulating target molecules present in optically dense media; this method is shown to be useful in limiting undesirable direct interaction of the probe radiation with the media itself, and provides a means for effectively exciting target molecular agents present in strongly absorbing or scattering matrices. Yeung et al. teach further use of non-linear optical excitation for highly specific excitation of target molecules present in very small volumes (M. J. Sepaniak and E. S. Yeung, "Laser Two-Photon Excited Fluorescence Detection for High Pressure Liquid Chromatography," Analytical Chemistry, 49 (1977) 1554–1556; M. J. Sepaniak and E. S. Yeung, "High-Performance Liquid Chromatographic Studies of Coal Liquids by Laser-Based Detectors," Journal of Chromatography, 211 (1981), 95–102; and W. D. Pfeffer and E. S. Yeung, "Laser Two-Photon Excited Fluorescence Detector for Microbore Liquid Chromatography," Analytical Chemistry, 58 (1986) 2103–2105). These works teach of the attractive performance advantages of non-linear optical excitation of target molecular agents present in complex matrices, specifically where reduced background excitation, low probe volumes, and complementary selection rules provided by non-linear methods aid in increasing selectivity of the analysis. Improved spatial control over the active region has been further developed by Wirth (M. J. Wirth and H. O. Fatunmbi, "Very High Detectability in Two-Photon Spectroscopy," Analytical Chemistry, 62 (1990) 973–976); specifically, Wirth teaches a method for achieving extremely high spatial selectivity in the excitation of target molecular agents using a microscopic imaging system. Similar control has been further applied by Denk et al. (W. Denk, J. P. Strickler and W. W. Webb, "Two-Photon Laser Microscopy," U.S. Pat. No. 5,034,613) who teach of a special confocal laser scanning microscope utilizing non-linear laser excitation to achieve intrinsically high three-dimensional control in the photo-activation of various molecular fluorophor agents on a cellular or sub-cellular scale. This microscope is used to excite molecular fluorophor agents added to biological specimens, which constitute an optically dense medium; the special properties of non-linear optical excitation are utilized to substantially limit excitation to a confocal region occurring at the focus of an objective lens, thereby allowing the possibility of three-dimensional imaging by sharply controlling the depth of focus. Control of photo-excitation for generation of luminescence-based images at the cellular and sub-cellular level is shown in target samples mounted on a stage. This microscope is also used for localized photolytic release of caged effector molecules present in individual cells mounted on a stage, and is claimed to be useful for inducing additional photochemical reactions in such cells. However, reduction in photo-induced necrosis of cells located at the focal plane is claimed to be the primary benefit of this microscopy approach, based on the replacement of ultraviolet excitation radiation with near infrared radiation.

While the substantial body of prior art exemplified by these cited examples clearly demonstrates many attractive features of photo-activation methods, a general method for achieving selective photo-activation of one or more molecular agents with a high degree of spatial control that is capable of meeting the diverse needs of industry has not been previously taught. Specifically, practical methods for effecting such control on scales that are significant for therapeutic uses or for general materials processing applications have not been previously taught.

Therefore, it is an object of the present invention to provide a method for the treatment of plant or animal tissue with a high degree of spacial selectivity.

It is further object of the present invention to provide such a method using a light source and photo-active materials to enhance the high degree of spacial selectivity.

It is another object of the present invention to provide such a method using wavelengths of light which are less harmful to the plant or animal tissue than the wavelengths of light currently used for the treatment of plant or animal tissue.

It is yet another object of the present invention to provide such a method using light which is less prone to scatter in and absorption by plant or animal tissue than the wavelengths of light currently used for the treatment of plant or animal tissue.

Consideration of the specification, including the several figures and examples to follow, will enable one skilled in the art to determine additional objects and advantages of the invention.

SUMMARY OF THE INVENTION

Having regard to the above and other objects and advantages, the present invention generally provides for a method for the treatment of a particular volume of plant or animal tissue comprising the steps of treating the plant or animal tissue with at least one photo-active molecular agent, wherein the particular volume of the plant or animal tissue retains at least a portion of the at least one photo-active molecular agent, and then treating the particular volume of the plant or animal tissue with light sufficient to promote a simultaneous two-photon excitation of at least one of the at least one photo-active molecular agent retained in the particular volume of the plant or animal tissue, wherein the at least one photo-active molecular agent becomes active in the particular volume of the plant or animal tissue.

The present invention also provides for a method for the treatment of cancer in plant or animal tissue comprising the steps of treating the plant or animal tissue with at least one photo-active molecular agent, wherein the cancer in the plant or animal tissue retains at least a portion of at least one of the at least one photo-active molecular agent, and treating the plant or animal tissue with light sufficient to promote a simultaneous two-photon excitation of the at least one photo-active molecular agent retained in the cancer in the plant or animal tissue, wherein the at least one photo-active molecular agent becomes active in the cancer in the plant or animal tissue.

The present invention further provides for a method for producing at least one photo-activated molecular agent in a particular volume of a material. The method comprises treating the particular volume of the material with light sufficient to promote a simultaneous two-photon excitation of at least one photo-active molecular agent contained in the particular volume of the material. The at least one photo-active molecular agent then becomes a photo-activated molecular agent in the particular volume of the material. In preferred embodiments of the present invention the material is selected from the group consisting of plant tissue and animal tissue and the material is pretreated with at least one photo-active molecular agent such that the material retains at least a portion of the photo-active agent at the time that the particular volume of the material is treated with light sufficient to promote a simultaneous two-photon excitation of the photo-active molecular agent.

The present invention also provides for a method for producing at least one photo-activated molecular agent in a particular volume of a material comprising treating the particular volume of the material with light sufficient to promote optical excitation of at least one photo-active molecular agent contained in the particular volume of the material, wherein the at least one photo-active molecular agent becomes a photo-activated molecular agent in the particular volume of the material.

In an additional preferred embodiment of the present invention, the light sufficient to promote a simultaneous two-photon excitation of the photo-active molecular agent is a laser light. It is further preferred that the laser is a pulsed laser light.

In another preferred embodiment of the present invention, the light sufficient to promote a simultaneous two-photon excitation of the photo-active molecular agent is a focused beam of light which is more preferably a focused laser light. It is further preferred that the focused laser light is a focused pulsed laser light.

In another preferred embodiment of the present invention, the photo-active molecular agent is selected from the group consisting of psoralen, psoralen derivatives, porphyrin derivatives, haematoporphyrin derivatives, tetraazaporphyrin derivatives, phthalocyanine derivatives, rhodamine derivatives, coumarin derivatives, benzophenoxazine derivatives, chlorpromazine, chlorpromazine derivatives, chlorophyll derivatives, bacteriochlorophyll derivatives, metal-ligand complexes, pheophorbide a, merocyanine 540, vitamin D, 5-amino-laevulinic acid, photosan, chlorin e6, chlorin e6 ethylenediamide, mono-L-aspartyl cholorin e6, and phenoxazine Nile blue derivatives.

It is more preferred that the photo-active molecular agent is selected from the group consisting of psoralen, 5-methoxypsoralen (5-MOP), 8-methoxypsoralen (8-MOP), 4,5',8-trimethylpsoralen (TMP), 4'-aminomethyl4,5',8-trimethylpsoralen (AMT), 5-chloromethyl-8-methoxypsoralen (HMT), angelicin (isopsoralen), 5-methylangelicin (5 -MIP), and 3-carboxypsoralen.

It is also more preferred that the photo-active molecular agent is selected from the group consisting of porphyrin, haematoporphyrin derivative (HPD), photofrin II, benzoporphyrin derivative (BPD), protoporphyrin IX (PpIX), dye haematoporphyrin ether (DHE), polyhaematoporphyrin esters (PHE), 13,17-N,N,N-dimethylethylethanolamine ester of protoporphyrin (PH1008), tetra(3-hydroxyphenyl) porphyrin (3-THPP), tetraphenylporphyrin monosulfonate (TPPS1), tetraphenylporphyrin disulfonate (TPPS2a), dihaematoporphyrin ether, meso-tetraphenyl-porphyrin, mesotetra(4N-methylpyridyl)porphyrin (T4MpyP), and octa-(4-tert-butylphenyl)tetrapyrazinoporphyrazine (OPTP).

It is further more preferred that the photo-active molecular agent is selected from the group consisting of phthalocyanine, tetra(4-tert-butyl)phthalocyanine ($t_4$-PcH$_2$), tetra-(4tert-butyl)phthalocyanatomagnesium ($t_4$-PcMg), chloroaluminum sulfonated phthalocyanine (CASPc), chloroaluminum phthalocyanine tetrasulfate (AlPcTS), monosulfonated aluminum phthalocyanine (A1SPc), di-sulfonated aluminum phthalocyanine (A1S2Pc), tri-sulfonated aluminum phthalocyanine (A1S3Pc), tetra-sulfonated aluminum phthalocyanine (A1S4Pc), silicon phthalocyanine (SiPc IV), zinc II phthalocyanine (ZnPc), bis(di-isobutyl octadecylsiloxy)silicon 2,3-naphthalocyanine (isoBOSINC) and germanium IV octabutoxy-phthalocyanine (GePc).

It is yet further preferred that the photo-active molecular agent is selected from the group consisting of rhodamine 101 (Rh- 101), rhodamine 110 (Rh-110), rhodamine 123 (Rh- 123), rhodamine 19 (Rh-19), rhodamine 560 (Rh-560), rhodamine 575 (Rh-575), rhodamine 590 (Rh-590rhodamine 610 (Rh-610), rhodamine 640 (Rh-640), rhodamine 6G (Rh-6G), rhodamine 700 (Rh-700), rhodamine 800 (Rh-800), rhodamine B (Rh-B), sulforhodamine 101, sulforhodamine 640, and sulforhodamine B.

It is still further preferred that the photo-active molecular agent is selected from the group consisting of coumarin 1, coumarin 2, coumarin 4, coumarin 6, coumarin 6H, coumarin 7, coumarin 30, coumarin 47, coumarin 102, coumarin 106., coumarin 120, coumarin 151, coumarin 152, coumarin 152A, coumarin 153, coumarin 311, coumarin 307, coumarin 314, coumarin 334, coumarin 337, coumarin 343, coumarin 440, coumarin 450, coumarin 456, coumarin 460, coumarin 461, coumarin 466, coumarin 478, coumarin 480, coumarin 481, coumarin 485, coumarin 490, coumarin 500, coumarin 503, coumarin 504, coumarin 510, coumarin 515, coumarin 519, coumarin 521, coumarin 522, coumarin 523, coumarin 535, coumarin 540, coumarin 540A, and coumarin 548.

In yet another preferred embodiment of the present invention, the photo-active molecular agent is selected from the group consisting of 5ethylamino-9-diethylaminobenzo[a]-phenoxazinium (EtNBA), 5-ethylamino-9-diethylaminobenzo[a]phenothiazinium (EtNBS), and 5 ethylamino-9-diethylaminobenzo[a]phenoselenazinium (EtNBSe). Additionally, it is preferred that the photo-active molecular agent is selected from the group consisting of tris(2,2'-bipyridine)ruthenium (II) dichloride (RuBPY), tris (2,2'-bipyridine)rhodium (II) dichloride (RhBPY), and tris (2,2'-bipyridine)platinum (II) dichloride (PtBPY).

Additionally, it is more preferred that the photo-active molecular agent is selected from the group consisting of stilbene, stilbene derivatives and 4-(N-(2-hydroxyethyl)-N-methyl)aminophenyl)-4'-(6hydroxyhexylsulfonyl)stilbene (APSS).

Further, it is more preferred that the at least one photo-active molecular agent includes at least one biogenic photo-active molecular agent, wherein the at least one biogenic agent includes a segment selected from the group consisting of DNA, RNA, amino acids, proteins, antibodies, ligands, haptens, carbohydrate receptors or complexing agents, lipid receptors or complexing agents, protein receptors or complexing agents, chelators, and encapsulating vehicles and yet further more preferred that the at least one biogenic photo-active molecular agent further includes a segment which is photo-activated when subject to light sufficient to promote a simultaneous two-photon excitation.

BRIEF DESCRIPTION OF THE DRAWINGS

Reference to the following detailed description of exemplary embodiments may help to better explain the invention. Consider the description in conjunction with the drawings in which:

FIG. 4 shows example excited state behavior for single-photon and two-photon photoionization;

DETAILED DESCRIPTION OF THE DRAWINGS

The invention described here utilizes the unique physical properties of non-linear optical excitation of molecular agents to effect improved spatial control over the photo-activation of those agents. In addition, non-linear optical excitation is shown to have further advantages during photo-activation of medical therapeutic and other agents, including reduction of collateral excitation and damage along the excitation path, reduction in exposure to harmful optical wavelengths, reduction of interference from absorption and scattering processes originating from the environment surrounding the excited agent, and enhanced molecular specificity in the excitation of the agent. The non-linear optical excitation method employed in this invention, referred to as simultaneous two-photon excitation, is shown to provide a superior means for the treatment of many diseases.

Energy Level Models of Linear and Non-linear Photo-activation Processes

The fundamental significance of the invention taught in this disclosure lies in the use of non-linear optical excitation processes to selectively photo-activate one or more molecular agent with a high degree of spatial control. This selective photo-activation is achieved by means of harnessing the special properties of non-linear optical excitation of an agent from one molecular energy level to another. To fully understand the salient features of this process, it is necessary to develop a conceptual model of non-linear, simultaneous two-photon excitation along with that for related linear and non-linear processes. This is most conveniently represented in the form of energy level diagrams.

Figure 1:
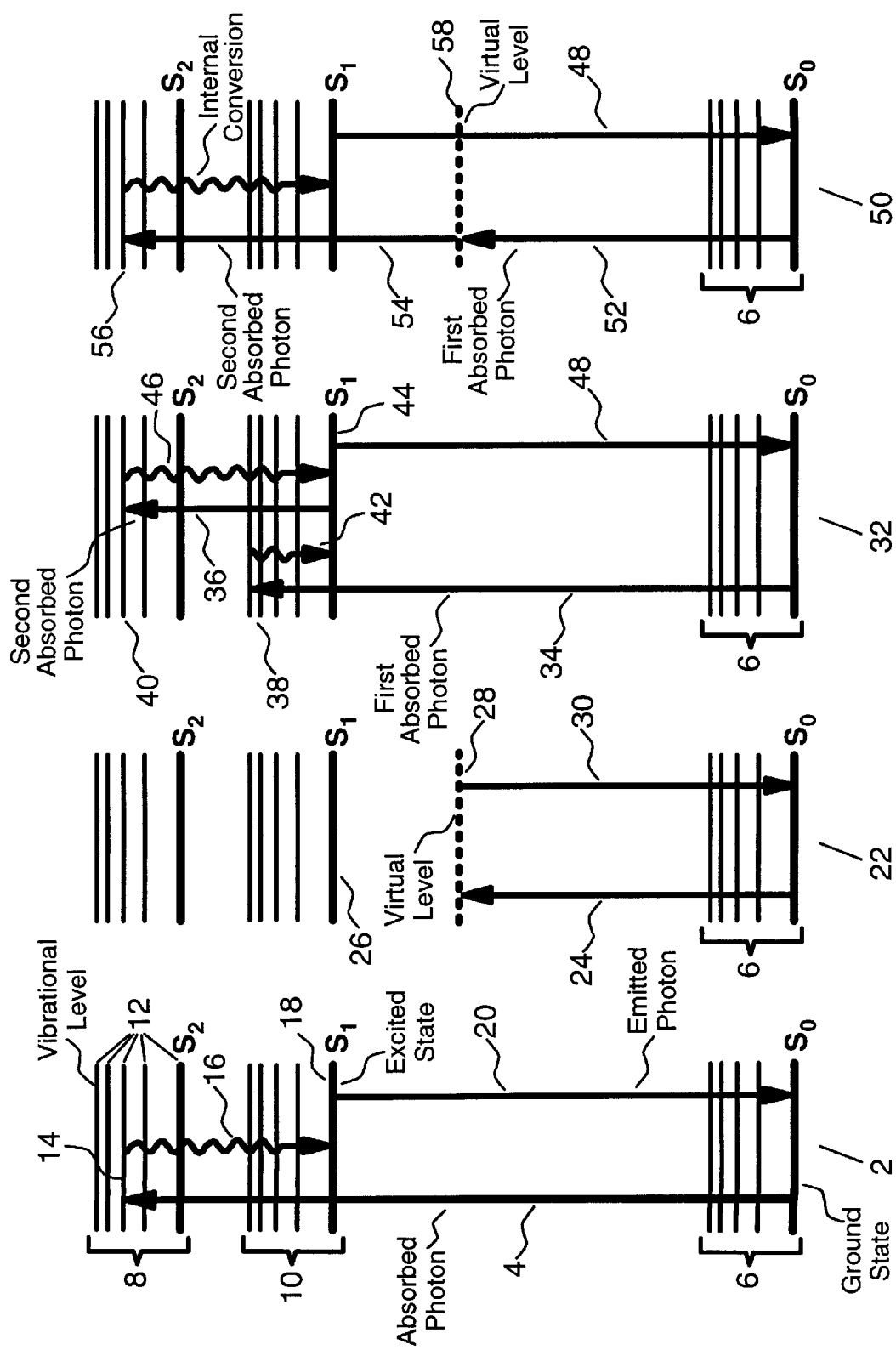
FIG. 1 shows example energy level diagrams for linear and non-linear optical excitation.

FIG. 1 shows typical molecular energy level diagrams for several linear and non-linear optical excitation processes. In this representation, which is a simplified Jablonski diagram, the vertical direction corresponds to a change in energy, while the horizontal direction represents the sequence of events, progressing from the left to right. Solid horizontal lines represent quantum mechanically allowed molecular energy levels, while dashed horizontal lines represent disallowed, virtual energy levels. Quantum mechanically allowed molecular energy levels are relatively long lived and the probability of excitation of a molecule upon absorption of energy, such as that provided by absorption of a photon of appropriate energy, is high. Virtual energy levels may be reached through a variety of excitation processes, but in contrast to allowed molecular transitions they have exceedingly short lifetimes (on the order of $10^{-15}$ s, as predicted by the Heisenberg uncertainty principle), making them significant only under special excitation conditions. Straight arrows in Jablonski diagrams represent radiative energy transfer processes: upward arrows indicate absorption of energy, while downward arrows represent radiative emission, such as fluorescent emission of a photon. Crooked arrows represent non-radiative energy transfer processes, such as vibrational relaxation. The vertical length of a straight or crooked arrow is proportional to energy absorbed or emitted in a given process.

For the first Jablonski diagram shown in FIG. 1, single-photon excitation to an allowed energy level 2 occurs upon absorption of a photon 4 having sufficient energy to directly promote the molecule from a first allowed electronic energy level 6 (generally the lowest electronic energy level, or ground state, called $S_0$) to a second allowed electronic energy level 8 having a higher overall energy level (represented here as the $S_2$ state). Note that there may be multiple allowed higher electronic energy levels to which excitation may occur, such as those represented by the second allowed electronic energy level 8 and the third allowed electronic energy level 10; these are typically denoted $S_1$, $S_2$, and so on as their energy increases. Also, each allowed electronic energy level may be further subdivided into an ensemble of discrete vibrational levels 12; each of these discrete vibrational levels 12 may in turn be further subdivided into an ensemble of discrete rotational energy levels. Hence, each allowed electronic energy level, $S_0$, $S_1$, $S_2$, and so on, constitutes a complex band of allowed energy levels due to the large number of possible vibrational and rotational states possible. Upon absorption of energy from a photon 4 the molecule is promoted to a particular unique electronic and vibrational level 14, sometimes referred to as a vibronic level. From this excited state the molecule can then undergo rapid internal conversion 16, for example to the lowest allowed excited vibronic energy level 18 in the third allowed electronic energy level 10, represented here as the $S_1$ state. This internal conversion 16 is typically very fast, occurring on a time scale on the order of $10^{-12}$ to $10^{-15}$ sec. Finally, the excited molecule can undergo further relaxation, such as through emission of a photon 20, to return to the initial, first energy level 6; possible relaxation processes include collisional deactivation, fluorescence and phosphorescence. An example of this process is promotion of the dye molecule coumarin from a ground electronic state to an excited electronic state through the absorption of a photon at 400 nm, followed by emission of a fluorescent photon at 480 nm. In this example the probability of excitation is linearly related to the power of the incident optical radiation, so single-photon excitation to an allowed energy level 2 is referred to as a linear excitation process.

For the second Jablonski diagram shown in FIG. 1, single-photon excitation to a virtual energy level 22 occurs upon absorption of a photon 24 having insufficient energy to directly promote the molecule to an allowed electronic energy level 26. Instead, the molecule is promoted to a very short lived virtual energy level 28. This virtual energy level 28 will typically have a lifetime on the order of $10^{-15}$ sec. Virtually instantaneous re-emission 30 of the absorbed photon 24 from this virtual level 28 will typically occur via processes such as elastic scatter. An important example of this process is Rayleigh scatter at 800 nm from coumarin upon excitation with light at 800 nm. Another example is Raman scatter, which occurs when the molecule returns to the various vibrational levels associated with the ground state. In these example processes the probability of excitation is also linearly related to the power of the incident optical radiation, so single-photon excitation to a virtual energy level 22 is also referred to as a linear excitation process.

For the third Jablonski diagram shown in FIG. 1, sequential two-photon excitation to an allowed energy level 32 occurs upon sequential absorption of a first photon 34 and a second photon 36, both of which have sufficient energy to directly promote the molecule from one allowed energy level to another allowed energy level. Upon absorption of the first photon 34, the molecule is promoted from a first allowed electronic energy level 6, such as the ground state $S_0$, to a second allowed electronic energy level 38, such as excited state $S_1$, from which the molecule typically can undergo rapid internal conversion 42 to a relatively long-lived lowest allowed excited vibronic energy level 44, with a lifetime typically on the order of $10^{-7}$ sec to $10^{-9}$ sec. Subsequent absorption of a second photon 36 while the molecule is still at this lowest allowed excited vibronic energy level 44 can promote the molecule to a third allowed electronic energy level 40, such as excited state $S_2$. The second photon 36 may have the same energy as the first photon 34, or the first photon 34 and second photon 36 may have different energies. Upon promotion to the third allowed energy level 40, the molecule may undergo a number of processes, including further internal conversion 46 and re-emission 48 of eneray. Alternatively, if the second photon 36 has sufficient energy, it may ionize the molecule through a photoionization process. An example of this process is photoionization of the dye coumarin upon very intense excitation with light at 440 nm to produce an ionized molecule, wherein the coumarin molecule sequentially absorbs two photons of light at 440 nm. In this third example the probability of excitation is not linearly related to the power of the incident optical radiation, but rather to the product of the powers of the first photon 34 and second photon 36; hence, sequential two-photon excitation to an allowed energy level 32 is referred to as a non-linear excitation process.

For the final Jablonski diagram shown in FIG. 1, simultaneous two-photon excitation to an allowed energy level 50 occurs upon simultaneous absorption of a first of two photons 52 and a second of two photons 54. In this case the combined energy of the first of two photons 52 and the second of two photons 54 is sufficient to promote the molecule from a first allowed energy level 6 to a second allowed energy level 56. Typically, the individual energies of neither the first of two photons 52 nor the second of two photons 54 is sufficient to directly promote this or any other allowed electronic transition. Instead, the first of two photons 52 promotes the molecule to a very short lived virtual energy level 58. This is the same virtual energy level as that shown in the second Jablonski diagram. Before relaxation can occur, the second of two photons 54 immediately promotes the molecule to a second allowed electronic energy level 56. The result is excitation that is equivalent to that achieved using linear single-photon excitation to an allowed energy level 2. Note that the first of two photons 52 and the second of two photons 54 may be of equal or unequal energy. Also, the instantaneous irradiance, or W m$^{-12}$, of the incident excitation light must be extremely high to yield significant efficiency in absorption of the second of two photons 54 before the virtual energy level 58 undergoes relaxation back to the original first allowed electronic energy level 6. In fact, because the lifetime of the virtual energy level 58 is on the order of $10^{-15}$ sec, pulsed excitation sources having very high peak powers are commonly used to efficiently stimulate these processes; such sources are often preferable since they are capable of providing large numbers of photons to the excited molecule during the brief lifetime of the virtual energy level 58. An example of the simultaneous two-photon excitation process is the promotion of the dye molecule coumarin from a ground electronic state to an excited electronic state through the simultaneous absorption of two photons at 800 nm, followed by emission of a fluorescent photon at 480 nm. In this fourth example the probability of excitation is related to the product of the instantaneous or peak powers of the first of two photons 52 and the second of two photons 54. This can be conceptualized in the form of a photochemical reaction, $$\text{Molecule}_{GROUNDSTATE} + 2h\nu_{800nm} \rightarrow \text{Molecule}_{EXCITEDSTATE} \quad (1)$$

which shows that a molecule in the ground state is promoted to an excited state following simultaneous absorption of two photons at 800 nm, $h\nu_{800\ nm}$. The reaction rate, R, is given by $R = k[\text{Molecule}_{GROUNDSTATE}][h\nu_{800\ nm}]^2$, where k is a rate constant and where $[\text{Molecule}_{GROUNDSTATE}]$ and $[h\nu_{800\ nm}]$ symbolize concentrations of the ground state molecule and the excitation photons, respectively. Hence, due to the well known quadratic dependence on instantaneous photon irradiance, simultaneous two-photon excitation to an allowed energy level 50 is also referred to as a non-linear excitation process.

It is important to understand a key difference between sequential two-photon excitation to an allowed energy level 32 and simultaneous two-photon excitation to an allowed energy level 50. In sequential two-photon excitation to an allowed energy level 32, the individual energies of both the first photon 34 and the second photon 36 must be appropriate to promote the molecule directly to the second allowed electronic energy level 38 and the third allowed electronic energy level 40. In contrast, simultaneous two-photon excitation to an allowed energy level 50 is more universal in that it requires only that the combined energy of the first of two photons 52 and the second of two photons 54 be sufficient to promote the molecule to a second allowed electronic energy level 56.

The invention taught here utilizes non-linear, simultaneous two-photon excitation to an allowed energy level 50. In succeeding portions of this disclosure, the simultaneous two-photon excitation to an allowed energy level 50 process is referred to as "simultaneous two-photon excitation". Where it is necessary to make a distinction between "simultaneous two-photon excitation" and sequential two-photon excitation to an allowed energy level 32, the term "sequential two-photon excitation" is used to describe the latter. Sequential two-photon excitation is useful for inducing photoionization of molecular agents, particularly under laboratory conditions, but has few significant commercial applications as a consequence of its several disadvantages, including difficulty in spatial control of application, and the need for excitation sources providing the necessary multiple photon energies.

Figure 2:
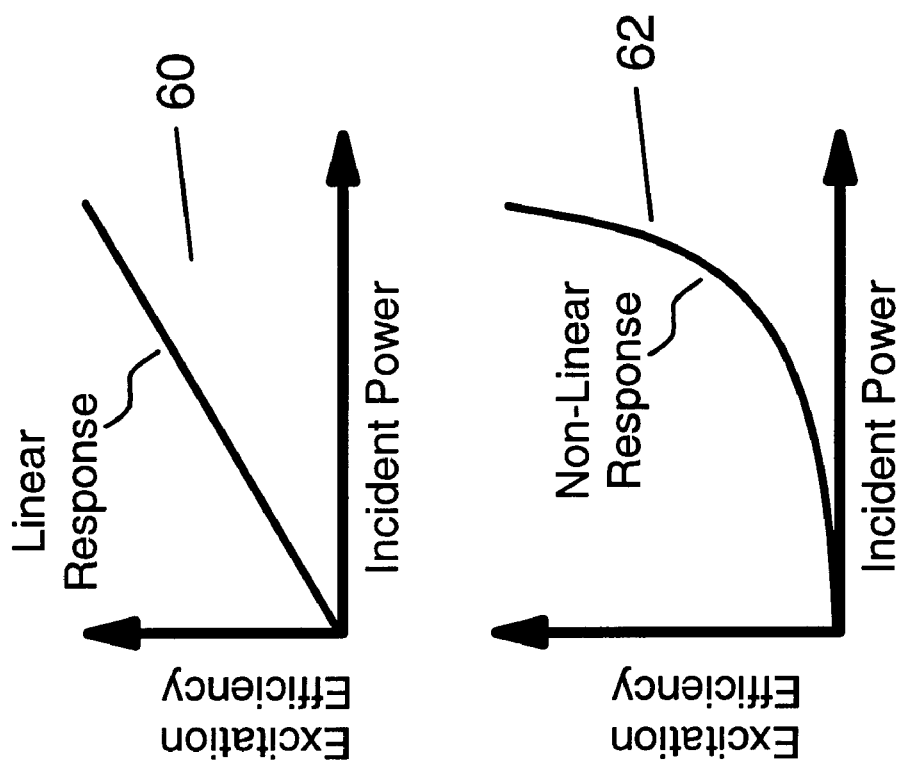
FIG. 2 shows the relationships between incident power and excitation efficiency for single-photon and two-photon excitation.

Comparison of Single-photon Excitation and Simultaneous Two-photon Excitation When light interacts with a molecular system, it induces a polarization that is proportional to the linear susceptibility multiplied by the magnitude of the applied electric field. When this electric field is very intense, the system cannot be described as easily, and higher order interaction terms must be included in the description of the induced polarization. Simultaneous two-photon excitation is referred to as a non-linear process because it occurs when the electromagnetic fields from two photons combine via these higher order terms, specifically the imaginary portion of the third-order susceptibility, $\chi^{(3)"}$, to induce an electronic transition. This is another way of describing the non-linearity of simultaneous two-photon absorption. That is, the molecular system is reacting non-linearly to the intense electromagnetic field. In contrast, single-photon excitation processes may be described by the linear susceptibility and are linear with excitation power. These disparate relationships between incident power and excitation efficiency are shown in FIG. 2 for single-photon excitation 60 and for simultaneous two-photon excitation 62. Note that the cross-section for simultaneous two-photon excitation is typically about a hundred thousand-fold smaller than that for an equivalent sinole-photon excitation process. This is due to the low probability that two photons will simultaneously interact with a molecule during the lifetime of the extremely brief virtual energy level. However, the availability of optical excitation sources capable of providing extremely high peak powers, such as mode-locked lasers, can substantially ameliorate the impact of this low efficiency by increasing instantaneous incident powers and thereby dramatically increasing the effective efficiency of simultaneous two-photon excitation. For example, when using continuous wave excitation the efficiency of two-photon excitation for a particular molecular system may be $10^5$ smaller than that achieved with single-photon excitation. However, if the same average optical power is emitted in the form of a train of very short pulses, the shift in product of the peak and average powers can change this ratio such that it is close to unity.

Figure 3:
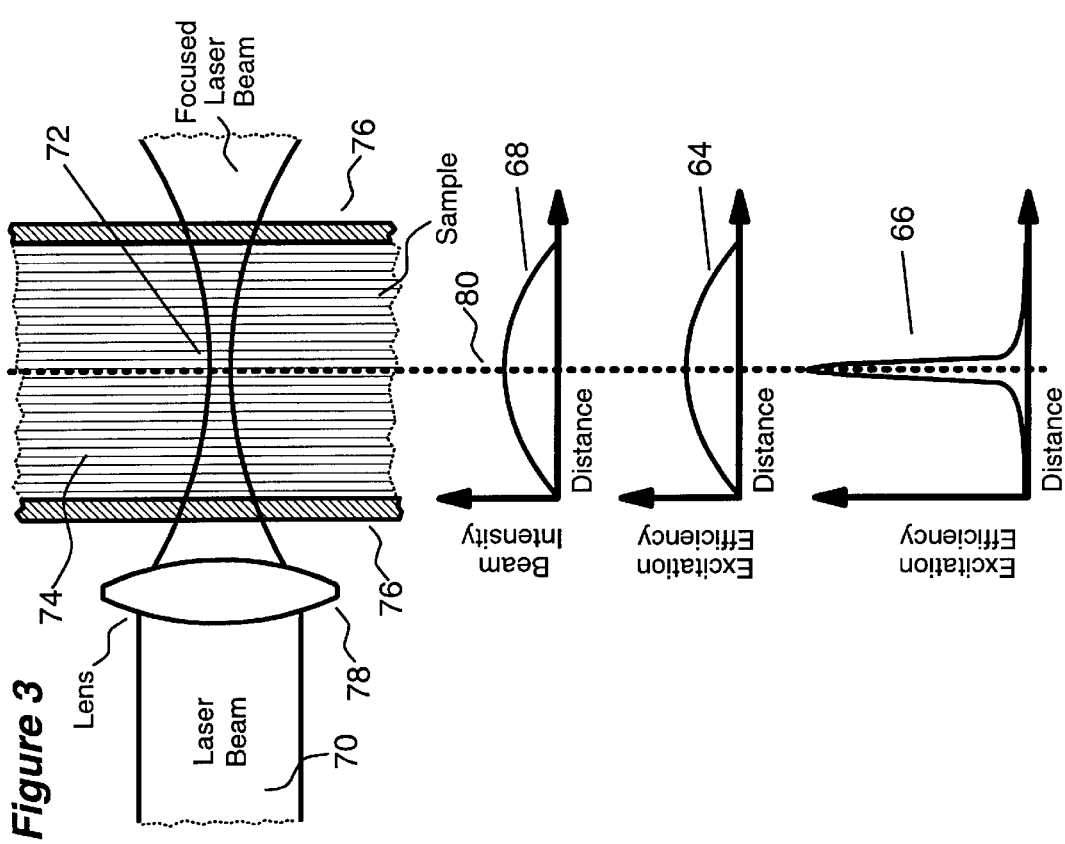
FIG. 3 shows a schematic representation of single-photon and two-photon photoionization.

The non-linear nature of simultaneous two-photon excitation can be exploited to achieve an important difference in the spatial excitation properties of simultaneous two-photon excitation and linear excitation. For example, FIG. 3 shows that the single-photon excitation efficiency profile 64 and the simultaneous two-photon excitation efficiency profile 66 can be made to differ dramatically as a function of the beam intensity profile 68 when a laser beam 70 is focused 72 into a material 74. This material 74 might be a laser dye solution held between the walls of a cuvette 76. Focussing 72 of the laser beam 70 with a lens 78 produces a beam intensity profile 68 that varies as a function of distance through the sample 74, reaching a maximum level at the center of the focus 80 as predicted by classical Gaussian optical theory. For a single-photon process, the linear relationship between beam intensity (or incident power) and excitation efficiency results in a single-photon excitation efficiency profile 64 that linearly follows the beam intensity profile 68. In contrast, for the simultaneous two-photon process, the non-linear relationship between beam intensity (or incident power) and excitation efficiency results in a simultaneous two-photon excitation efficiency profile 66 that follows the square of the beam intensity profile 68. Hence, focussing 72 the laser beam 70 can be used to substantially limit the extent of excitation to a small focus zone when simultaneous two-photon excitation is employed. This is sometimes referred to as the confocal region, and is defined as the zone extending a distance of $2\pi w_0^2/\lambda$, where $w_0$ is the diameter of the minimum beam waist and $\lambda$ is the wavelength of the optical radiation. In contrast, when linear excitation is employed, excitation occurs substantially along the entire optical path, making spatial localization of excitation considerably less defined.

Once a molecule has been promoted to an excited state, a variety of physical or chemical processes may occur, including luminescent emission of a photon, photochemical transformation, such as isomerization or oxidation, or photoionization. Importantly, it is the fundamental properties of the excited state and its environment that determine the ultimate fate of the molecule. The mechanism responsible for promoting the molecule to the excited state has no significant impact on this fate since the excitation process itself does not directly impact the subsequent properties of the excited molecule or its environment.

Equivalency in excited state behavior is shown schematically in FIG. 4 (in Jablonski diagram form) for single-photon photoionization 82 and simultaneous two-photon photoionization 84 of a molecular agent, such as perchloroethylene. In single-photon photoionization 82 absorption of energy from a single photon 86 promotes a molecule from its ground state 88 to an energy level at or above the ionization potential 90 of the molecule. This ionization potential 90 will be above the normal excited state energy levels 92. Upon promotion to an energy level at or above the ionization potential 90 by absorption of the single-photon 86, the molecule will undergo photoionization 94, here designated as the reaction, R→R+, where R is the initial form of the molecule and R+ is the ionized form of the molecule. For the molecule perchloroethylene, photoionization 94 can occur upon the absorption of a single photon 86 at 254 nm (4.88 eV). In simultaneous two-photon photoionization 84, simultaneous absorption of energy from a first of two photons 96 and a second of two photons 98 occurs. If the combined energy of these first of two photons 96 and second of two photons 98 is equal to that of the energy of the single photon 86 absorbed in the single-photon photoionization 82 example, the effect on the molecule is identical. The first of two photons 96 promotes the molecule to a virtual energy level 100, from which it is immediately promoted to an energy level at or above the ionization potential 90 by absorption of the additional energy provided by the second of two photons 98. Once excitation has occurred, photoionization 94 proceeds in an identical manner to that shown for single-photon excitation 82. For the example of perchloroethylene, simultaneous absorption of a first of two photons 96 at 508 nm (2.44 eV) and a second of two photons 98 at 508 nm (2.44 eV) results in photoionization 94 that is identical to that which would occur if a single photon at 254 nm (4.88 eV) was absorbed.

Note that in addition to the example energy level diagrams shown in FIG. 1 and in FIG. 4, many other possible transitions and energy level conditions are possible, depending upon numerous factors, including the characteristics of the molecular system, its environment, and the particular energies of the absorbed and released forms of energy, along w,ith their temporal and spatial correlations. For example, an important transition omitted for the sake of clarity from FIG. 1 or FIG. 4 is intersystem crossing from a singlet excited state to a triplet excited state. This transition is particularly important in luminescent processes and in many photochemical processes. The singlet electronic transitions shown in FIG. 1 and in FIG. 4, such as $S_0 \to S_2$, constitute quantum mechanically allowed transitions according to the Pauli exclusion principle, where the spins of all electrons remain paired and these paired electron spins are opposite to one another. A triplet state differs from a singlet state in that the electron in the higher energy level has the same spin orientation as the electron in the lower energy level. While such singlet-triplet transitions are quantum mechanically forbidden, the probability of internal conversion is greater than zero for some molecular systems as a consequence of the relatively long lifetime of the $S_1$ state compared to the intersystem crossing rate constant. Since the transition from the triplet state back to a singlet state is also forbidden, such as $T_1 \rightarrow S_0$, the lifetime of triplet excited states can be especially long, typically ranging from $10^{-6}$ to $10^1$ sec. This is important, because this long triplet state lifetime can allow an excited molecule to undergo a variety of chemical reactions, especially those involving energy transfer to another molecule. Reactions involving triplet state intermediates are particularly important in the photochemistry of many large organic or bio-organic molecules, and serves as a major mechanistic step in the photo-activation of many molecular agents used for photodynamic therapy.

Figure 5:
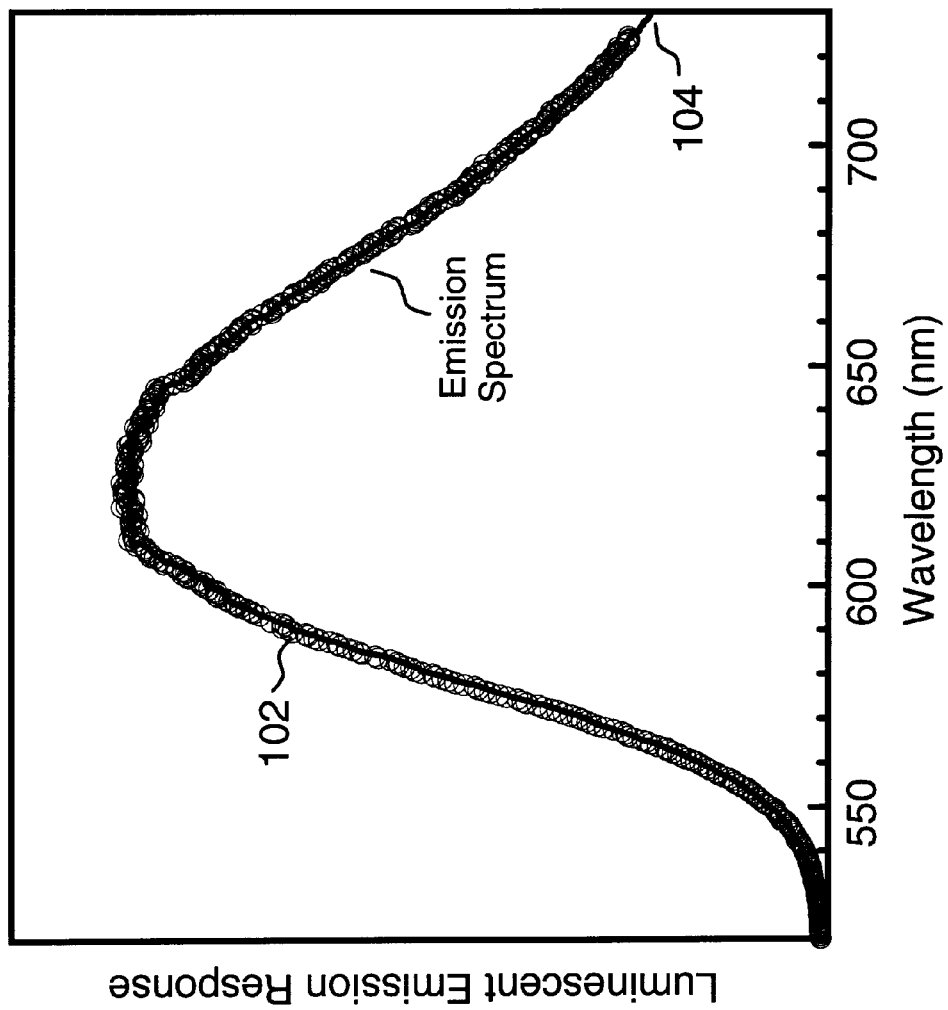
FIG. 5 compares luminescent emission properties of the molecule RuBPY as a function of emission wavelength for single-photon excitation and for simultaneous two-photon excitation.

The foregoing discussion on equivalence of excited state behavior can be expanded to include those cases involving triplet excited states, since the pathways for molecular excitation, reaction, and emission, including those involving triplet states, are determined by the molecule and its environment. Hence, a molecule that undergoes a specific photochemical or photophysical transformation upon promotion to a triplet excited state will experience the same transformation regardless of whether it has been excited by a single-photon process or by a simultaneous two-photon process. As an example, we have shown that the metal-ligand complex tris(2,2'-bipyridine)ruthenium (II) dichloride (RuBPY) exhibits identical excited state properties upon single-photon excitation at 390 nm or simultaneous two-photon excitation at 780 nm (where the combined energy of the two photons at 780 nm is equivalent to one photon at 390 nm). FIG. 5 compares the luminescent emission properties of RuBPY as a function of emission wavelength following single-photon excitation 102 at 390 nm, shown as circles, and following simultaneous two-photon excitation 104 at 780 nm, shown as a solid line. The emission properties from the triplet excited state are identical for the two methods, indicating that the excited state and its subsequent properties are identical and are independent of excitation method.

Figure 6:
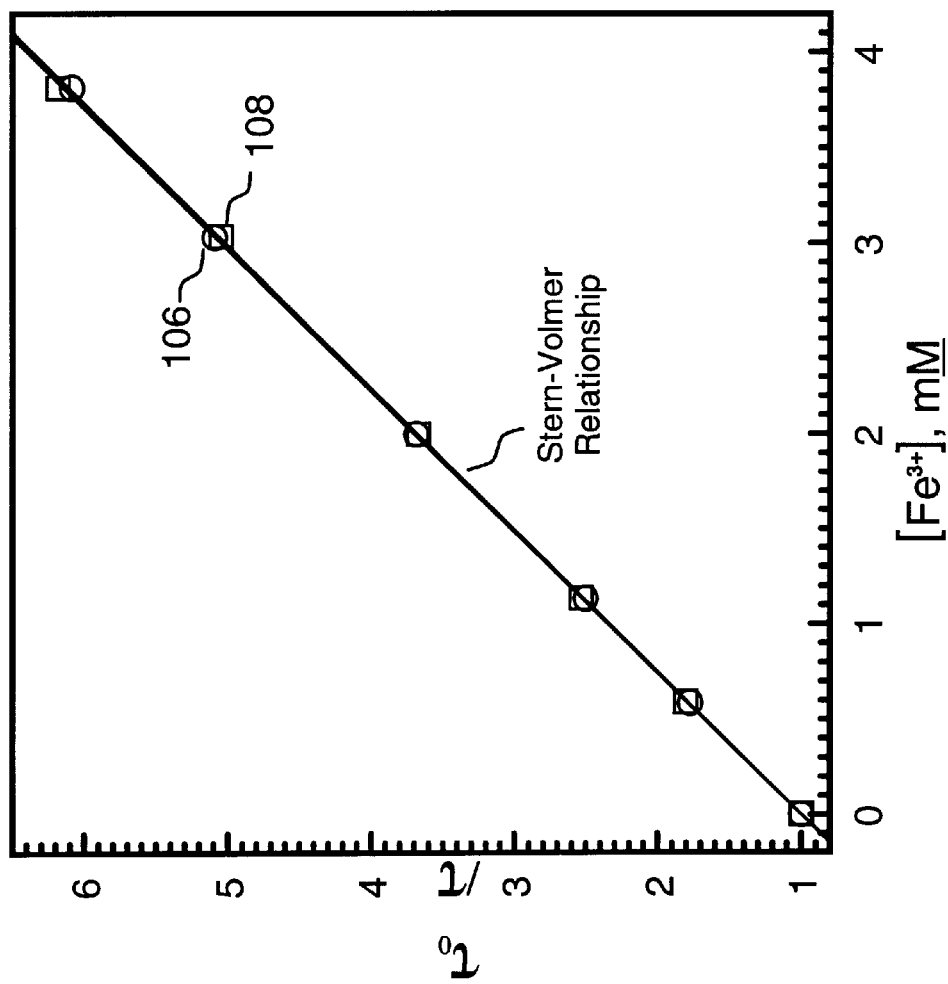
FIG. 6 is a Stern-Volmer plot of luminescent emission lifetime as a function of excited state quencher concentration.

As a further confirmation of this equivalence in excited state behavior, FIG. 6 shows that if the luminescent emission lifetimes of RuBPY are measured using single-photon excitation 106 at 386.5 nm, shown as circles, and using simultaneous two-photon excitation 108 at 782 nm, shown as squares, identical excited state properties are again observed. Specifically, FIG. 6 is a Stern-Volmer plot of luminescent emission lifetime as a function of excited state quencher concentration. When a molecule is promoted to an excited state, the length of time, $\tau$, that it resides at the excited state is determined by the fundamental properties of the molecule, and is defined as $\tau = \tau_0$. If an excited state quencher is added to the system, this lifetime will change to a different value of $\tau$. It is well known that when the ratio of $\tau_0/\tau$ is plotted as a function of excited state quencher concentration, a linear relationship is to be expected. This is referred to as a Stern-Volmer plot. FIG. 6 shows that for an aqueous RuBPY solution having different amounts of added $Fe^{3+}$ quencher, the Stern-Volmer plots for single-photon excitation 106 and for simultaneous two-photon excitation 108 are identical. This further confirms that the excited state properties of a molecule are identical, and that they are independent of the mechanism responsible for promotion to the excited state.

Figure 7:
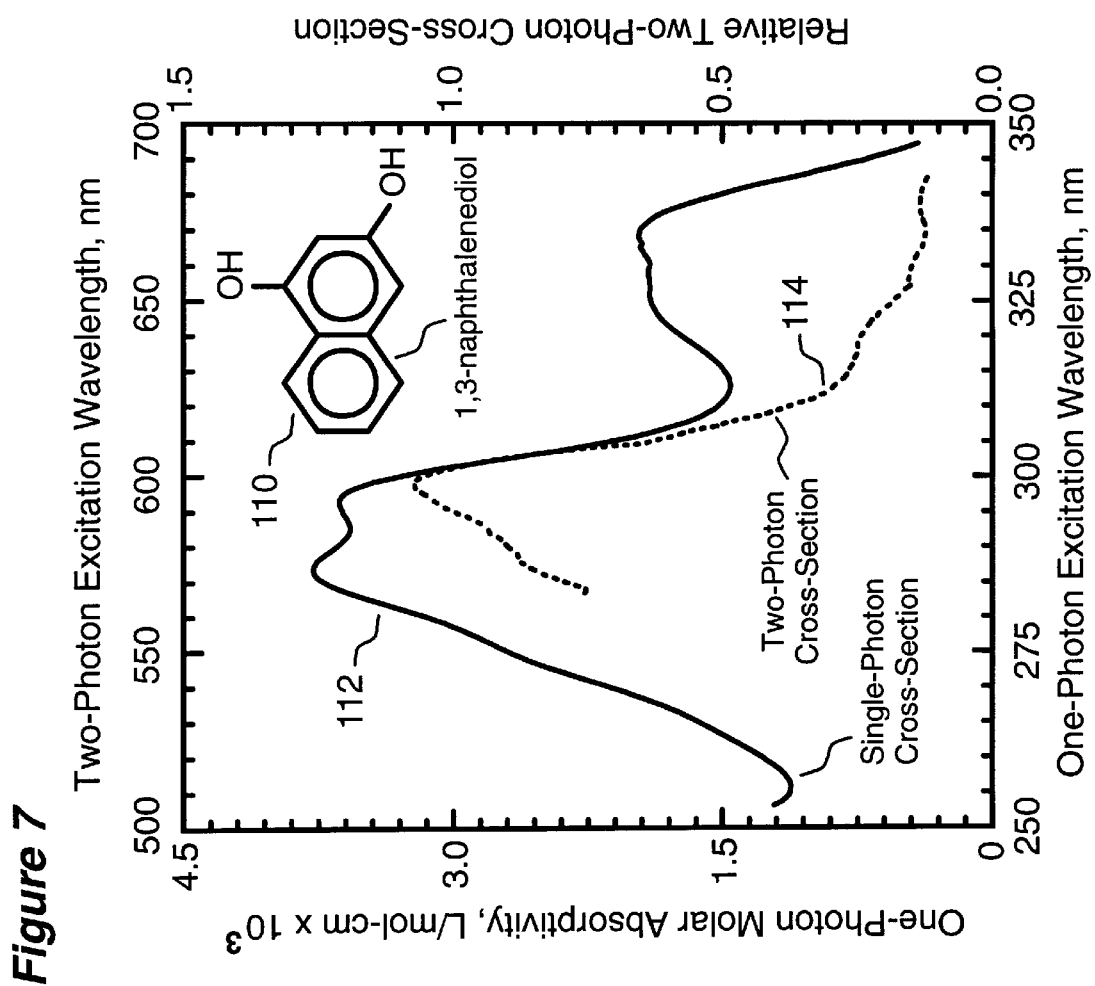
FIG. 7 compares absorption cross-sections as a function of excitation wavelength for 1,4-naphthalenediol when using single-photon excitation and simultaneous two-photon excitation.

The selection rules and cross-section for the excitation process may be vastly different for single-photon and simultaneous two-photon excitation, yet the properties of a specific excited state of a molecule are the same regardless of the excitation mechanism used to promote the molecule to that excited state. FIG. 7 provides a relative comparison of absorption cross-sections as a function of excitation wavelength for 1,3-naphthalenediol 110 when using single-photon excitation 112 and simultaneous two-photon excitation 114. Note that the wavelength scale for the data representing simultaneous two-photon excitation 114 has been scaled to reflect that simultaneous two-photon absorption is equivalent in energy to absorption of a single photon at twice the energy (or one half the wavelength) of the each of two photons. Comparison of the relative cross-sections for single-photon excitation 112 and for simultaneous two-photon excitation 114 of 1,4-naphthalenediol 110 show significant differences as a function of wavlength. These differences in cross-section are attributable to differences in one-photon and two-photon selection rules for particular molecular transitions, and may be useful for optimizing selectivity of excitation based on the differences in one- and two-photon selection rules, or in designing specific molecular agents with special two-photon absorption properties. In general, however, while there may or may not be significant differences in these selection rules and cross-sections for specific molecular agents, the excited state properties of these specific molecular agents will be substantially identical at each effective excitation wavelength regardless of excitation method.

Figure 8:
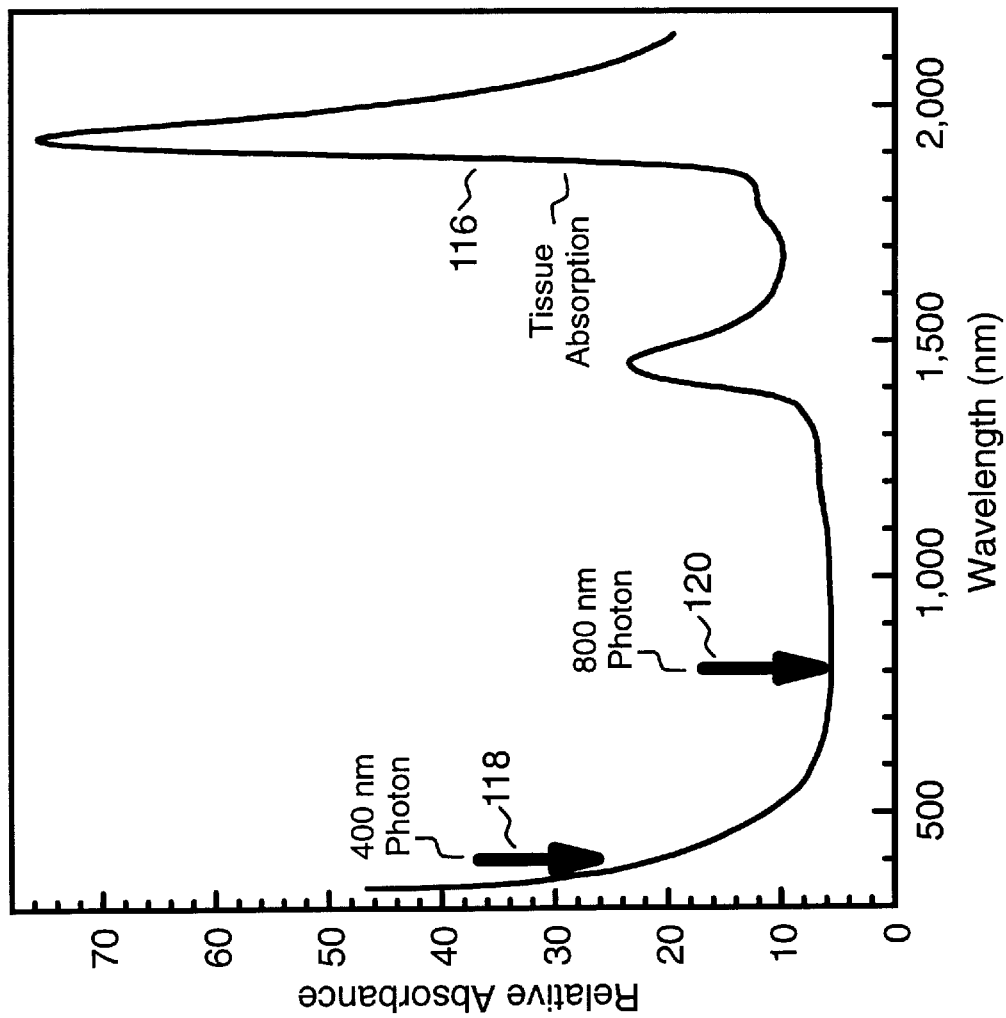
FIG. 8 shows an example absorption spectrum for animal tissue covering the ultraviolet to near infrared spectral region.
Figure 9:
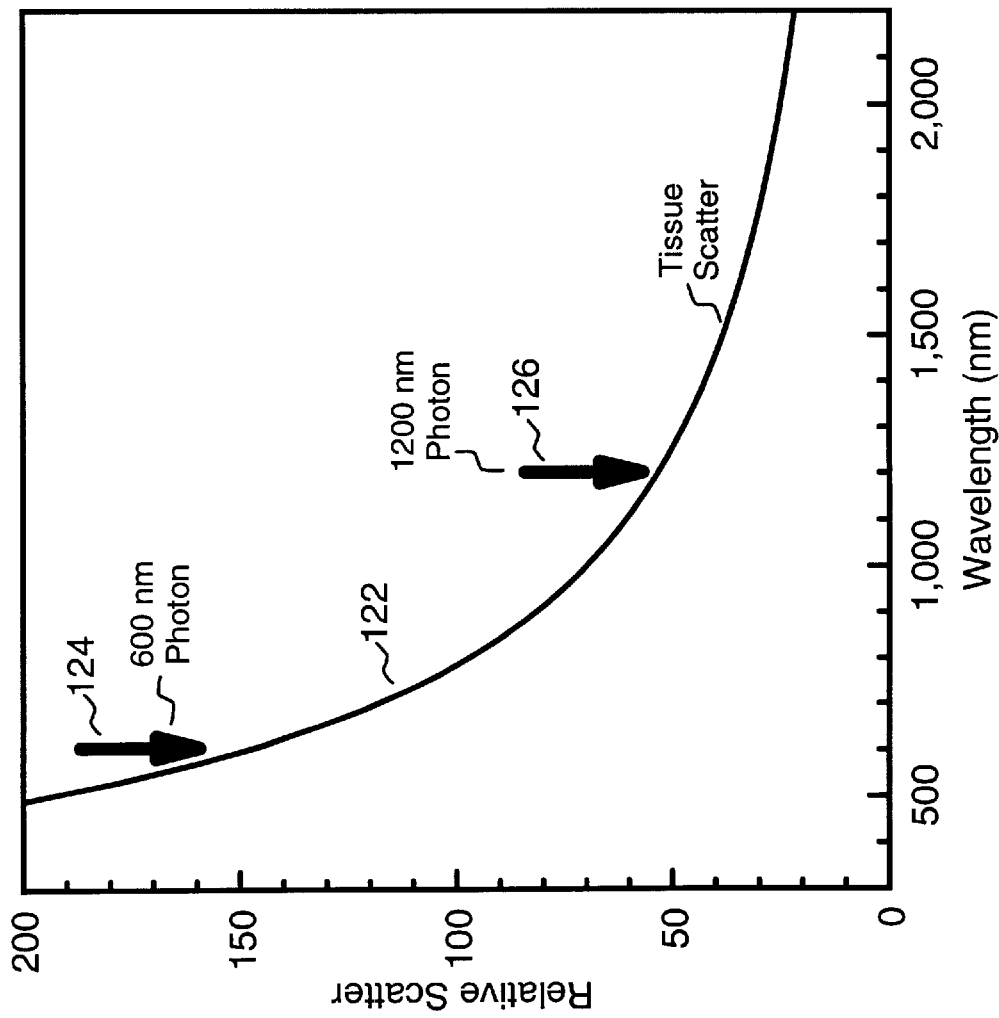
FIG. 9 shows a scattering spectrum for animal tissue covering the ultraviolet to near infrared spectral region.

Significance of Absorbance and Scattering Properties in Single-photon and Smultaneous Two-photon Processes While the cross-section for simultaneous two-photon excitation may be considerably lower than that observed with single-photon excitation, use of the simultaneous two-photon method may be favorable to single-photon excitation under many conditions because of lower matrix absorption and optical scattering of longer wavelength optical radiation. For example, FIG. 8 shows an absorption spectrum 116 for animal tissue, such as human dermis, covering the ultraviolet (UV) to near infrared (NIR) spectral region. FIG. 9 shows a scattering spectrum 122 for animal issue, such as human dermis, under similar conditions. Specifically, FIG. 8 demonstrates how higher-energy photons 118 may experience considerably greater tissue absorption than lower-energy photons 120. For instance, human skin strongly absorbs higher-energy photons 118 at 400 nm, but is relatively transparent to lower-energy photons 120 at 800 nm. This is a consequence of the natural absorbance of higher-energy photons 118 by pigments, proteins, and genetic materials, among other natural components, of skin. FIG. 9 further demonstrates how higher-energy photons 124 may experience considerably greater tissue scatter than lower-energy photons 126. Any optically dense medium, such as human skin, will strongly scatter higher-energy photons 124, for example at 600 nm, but will exhibit much lower scatter for lower-energy photons 126 at 1200 nm. These differences in optical properties have two important consequences. First, absorption of short-wavelength, higher-energy photons 118 by tissue can result in undesirable tissue damage upon exposure to UV or other high-energy light. In contrast, negligible effects may be experienced under irradiation with lower-energy photons 120, such as NIR light, even when the optical power of the NIR light is many-fold higher than that of the UV radiation. Secondly, the inherently high absorption and scatter of higher-energy photons 118 by tissue can result in very shallow tissue penetration depths, while lower-energy photons 120 generally have much greater penetration depths.

Figure 10:
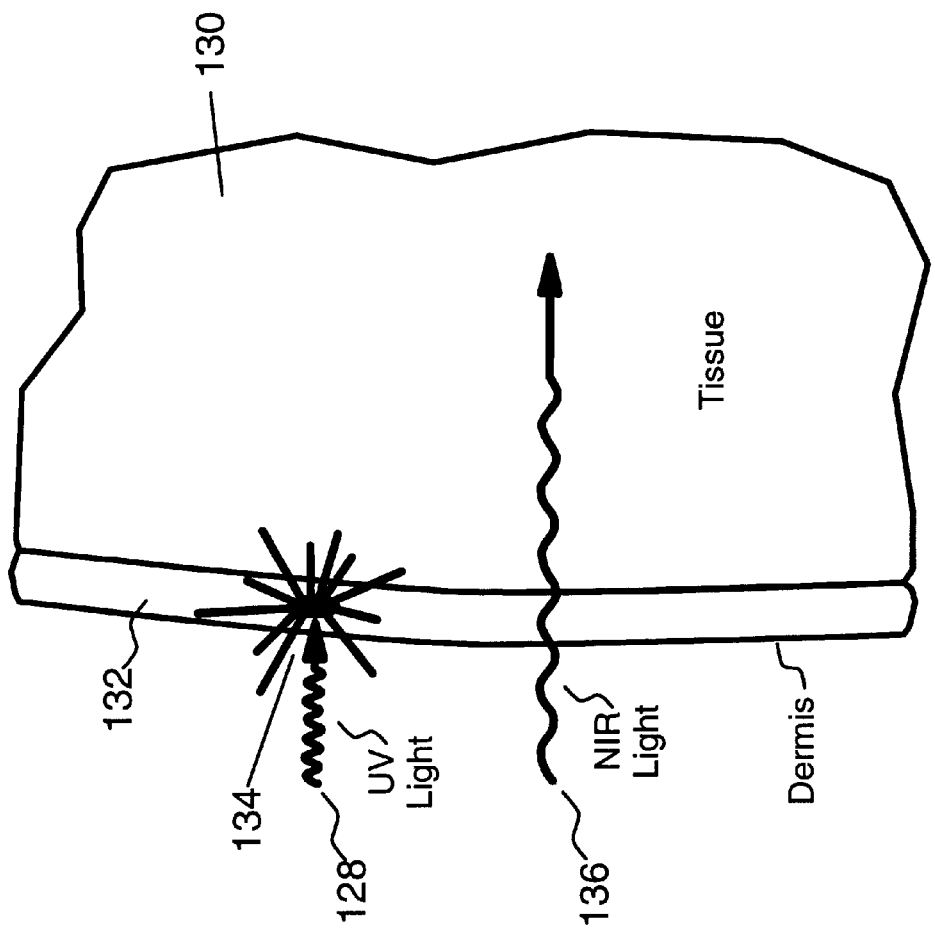
FIG. 10 shows the general trends in optical absorption properties of animal tissue for short wavelength and long wavelength light.

These important differences in absorption and penetration depth properties for higher-energy and lower-energy light are shown schematically in FIG. 10. When UV light 128, for example light at 400 nm, impinges on human tissue 130, the majority of the optical energy is immediately absorbed and scattered in the outermost layers 132, such as the epidermis and dermis. Absorption may occur due to excitation of certain molecules in the cells of this tissue 130, such as those composing the genetic material in the cellular nucleus. This absorption of higher-energy light by cellular constituents can thereby initiate a variety of collateral photochemical changes 134 in these cells. These collateral photochemical changes 134 resulting from absorption of UV light 128 can include irreversible genetic damage and induction of cancer. In contrast, NIR light 136, for example at 800 nm, will not be appreciably absorbed or scattered by tissue 130. The overall depth of penetration will be much greater and the extent of collateral damage to cells will be substantially lower. Hence, if long-wavelength excitation light is used to replace higher-energy, single-photon excitation, it is possible to photo-activate specific molecules using relatively non-damaging, high penetration depth simultaneous two-photon excitation methods.

Figure 11:
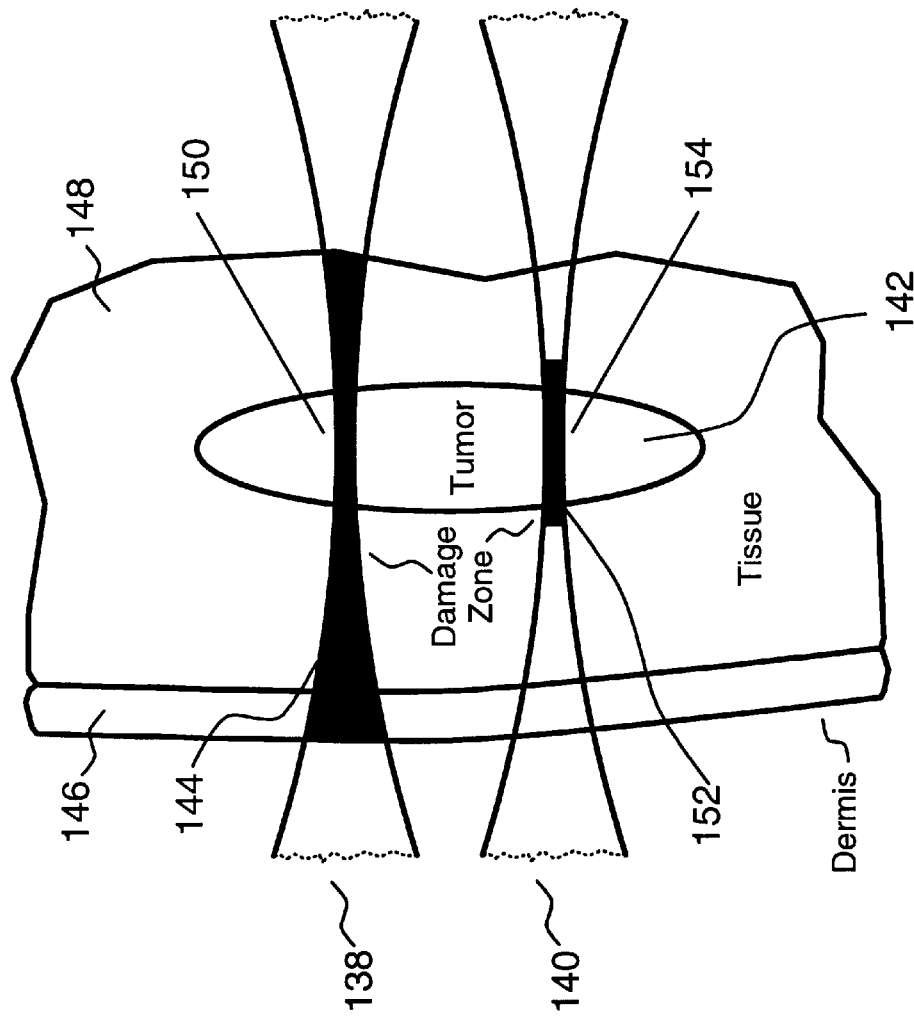
FIG. 11 compares optically-induced damage in tissue when single-photon and two-photon excitation methods are used.

Furthermore, the properties of non-linear excitation shown in FIG. 3 have additional implications when coupled with the inherent non-damaging nature and low absorption of NIR light. For example, FIG. 11 compares the extent of optically-induced damage in tissue when single-photon excitation 138 and simultaneous two-photon NIR excitation 140 methods are used to irradiate a subcutaneous tumor 142. Single-photon excitation 138 produces a photodamage zone 144 that extends substantially along the entire optical path and has no significant biospecificity. Hence, in addition to induction of the desired photodamage in the tumor 142, collateral damage can occur throughout surrounding tissues, such as the epidermis 146 and the surrounding dermis 148. If the single-photon excitation 138 is focussed, the photodamage zone 144 will be slightly enhanced at the focus 150. Note, however, that this photodamage zone 144 might not even extend into the tumor 142 if the UV or visible lioht is absorbed by the epidermis 146 and dermis 148 prior to reaching the tumor 142. This can occur as a consequence of the inherently high absorptivity of tissue at short wavelengths. In contrast, use of NIR simultaneous two-photon excitation 140 produces a sharply defined remote photodamage zone 152 that is substantially localized to the focus 154 as a consequence of the non-linear properties of this excitation method. Furthermore, because tissue does not appreciably absorb NIR light, collateral damage to the surrounding epidermis 146 and dermis 148 is minimized.

Figure 12:
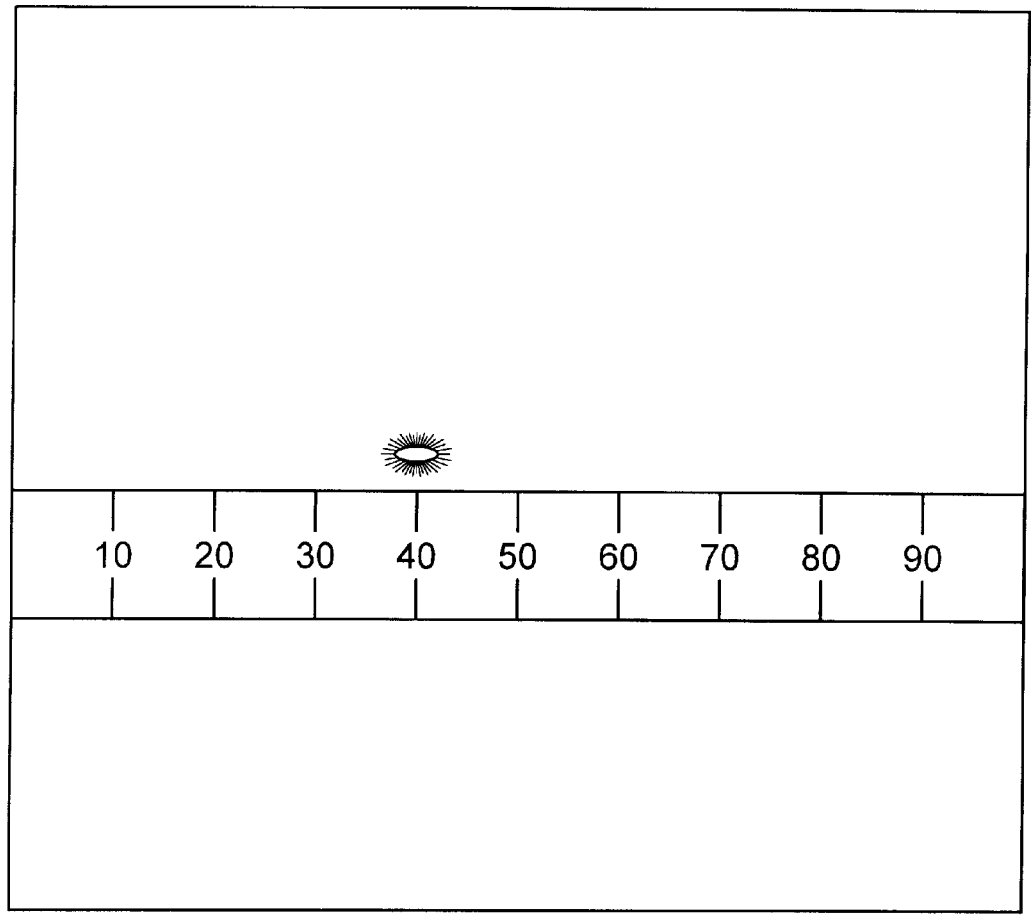
FIG. 12 shows a photograph of two-photon excited fluorescence of the dye molecule coumarin 480 distributed evenly throughout a block of agarose gelatin.
Figure 13:
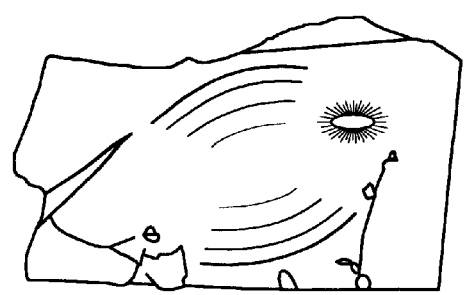
FIG. 13 shows a photograph of two-photon excited fluorescence of the dye molecule coumarin 480 distributed evenly throughout a tumor specimen.

Stimulation of a localized, remote photo-activated response in an optically dense medium is demonstrated in FIG. 12. This shows a photograph of two-photon excited fluorescence of the dye molecule coumarin 480 distributed evenly throughout a block of agarose gelatin. NIR output of a mode-locked titanium:sapphire laser, which emitted a continuous train of 730 nm wavelength, <200 fs pulses of light at a 78 MHz pulse repetition frequency in a beam approximately 1 mm in diameter, was expanded to produce a collimated beam approximately 50 mm in diameter using a beam expanding telescope. This expanded beam was then focused into the gelatin block using a 100 mm focal length (f.l.), 50 mm diameter biconvex singlet glass lens. The gelatin block was then positioned such that the focus of this 100-mm f.l. lens fell at a position 40 mm into the block. FIG. 12 clearly shows that fluorescence from the coumarin 480 is only stimulated at the focus of the NMR beam. Because of the quadratic relationship between two-photon excitation and instantaneous laser power, molecular stimulation at positions along the beam path prior to and following the focus is negligible. Hence, little or no collateral photo-activation occurs outside the focus region. Also, because the NIR excitation light is only weakly scattered by the gelatin, sharp focus is maintained at deep penetration depths into the block. Note that the sharpness of the focus is determined by Gaussian optical properties; hence, the length of the focus region is easily adjusted by changing the optical parameters used for beam expansion and subsequent focusing. Similar results are obtained if an equivalent process is applied to a labeled tumor specimen, as shown in FIG. 13. This shows a photograph of two-photon excited fluorescence of the dye molecule coumarin 480 distributed evenly throughout a block of mouse carcinoma tissue. As in FIG. 12, a tightly localized site of activation is demonstrated.

Therapeutic Applications of Simultaneous Two-photon Excitation

The foregoing discussion suggests that the fundament differences in the absorption of UV and NIR light by tissue and cellular constituents, coupled with the special non-linear properties of simultaneous two-photon excitation, should have direct applicability for improvements in the treatment of disease, specifically in the field of photodynamic therapy (PDT). Conventional PDT, or more recently developed "two-photon" PDT methods, utilize optical energy to semi-selectively photo-activate photosensitive pharmaceutical agents that have been administered to diseased tissue. The route for administration of these agents is typically topical application to a diseased tissue or via systemic administration. Under ideal conditions, the PDT agents will partition into or otherwise become concentrated on or in the diseased tissue. This concentration may be a consequence of isolated topical application directly onto a superficial lesion, or through differences in the physical or chemical properties of the lesion which lead to partitioning of the PDT agent into the lesion. Following administration of the PDT agent, optical radiation is used to excite photochemical changes in the PDT agent that lead to a therapeutic effect. Alternatively, two or more agents may be administered to diseased tissue, where at least one is directly excited by interaction with light, and where the excited agent or agents is capable of transferring this captured energy via an energy transfer process (such as charge transfer or optical re-emission) to one or more of the other co-located agents to produce a therapeutic effect. An example is the use of a dye molecule in conjunction with a PDT agent, wherein the dye molecule captures the activating light, then transfers this energy to the PDT agent, thereby initiating a biological effect. In all cases, it is hoped by PDT practitioners that these photochemical changes will lead to localized cessation of cell proliferation or cell necrosis in the lesion.

Existing PDT excitation methods are based on a variety of methods that are substantially equivalent to those shown in FIG. 1, using either direct single-photon excitation 2 or sequential two-photon excitation 32; the latter method is the basis for all previously taught "two-photon" PDT methods described in the technical and patent literature. In both of these broad classes of excitation method, the common reliance on relatively high-energy, short-wavelength light results in short penetration depths and high potential for collateral tissue damage. For example, PDT therapy for esophageal cancer is effective for treatment of superficial lesions, but is much less effective for lesions that are not topically exposed. Also, PDT therapy for psoriasis based on 8-methoxypsoralen (8-MOP) has proven effective when UV irradiation is used to excite 8-MOP at wavelengths from about 250 to 400 nm, but this same UV radiation has been strongly linked to the development of skin cancer in surrounding areas. New PDT agents that are photo-activated using NIR light are being developed in an effort to circumvent the hazards associated with UV irradiation; in most cases these agents have proven to be relatively unstable and are often relatively toxic. This may be attributable in part to the lower activation thresholds of these agents, making them more susceptible to spontaneous or otherwise undesirable reactions outside the intended treatment zone. Other disadvantages of conventional PDT methods include poor specificity over the site of application and potential necrosis of healthy tissue along the optical excitation path.

The simultaneous two-photon excitation PDT method taught in this invention is capable of circumventing these limitations and complications associated with conventional PDT methods, and is compatible with existing PDT pharmaceutical agents along with the new class of NIR-activated PDT agents. Specifically, this invention enables improved localization in the photo-activation of PDT agents with significantly reduced potential for collateral tissue damage compared with that possible using conventional methods. Where control of penetration is not critical, un-focussed NIR light may be used to stimulate simultaneous two-photon photo-activation of PDT agents present in a relatively large irradiated area. In this case, the extent of PDT agent photo-activation is controlled by varying the location, intensity and duration of exposure to the NIR beam. Where precise control of penetration depth or volume extent of therapeutic application is more critical, focussed NIR light is used to stimulate the simultaneous two-photon photo-activation process. In this case, beam irradiance, exposure duration, and degree of focussing are used to control the extent of PDT agent photo-activation. In both cases, high-irradiance NIR radiation may be used to achieve maximum efficacy. Furthermore, the high penetration depths achievable with NIR radiation combined with the inherent localization of photo-activation that is possible with focused simultaneous two-photon excitation provide a unique means for photo-activating PDT agents in subsurface lesions without damaging overlying or underlying healthy tissues.

First Exemplary Embodiment of the Invention

Figure 14:
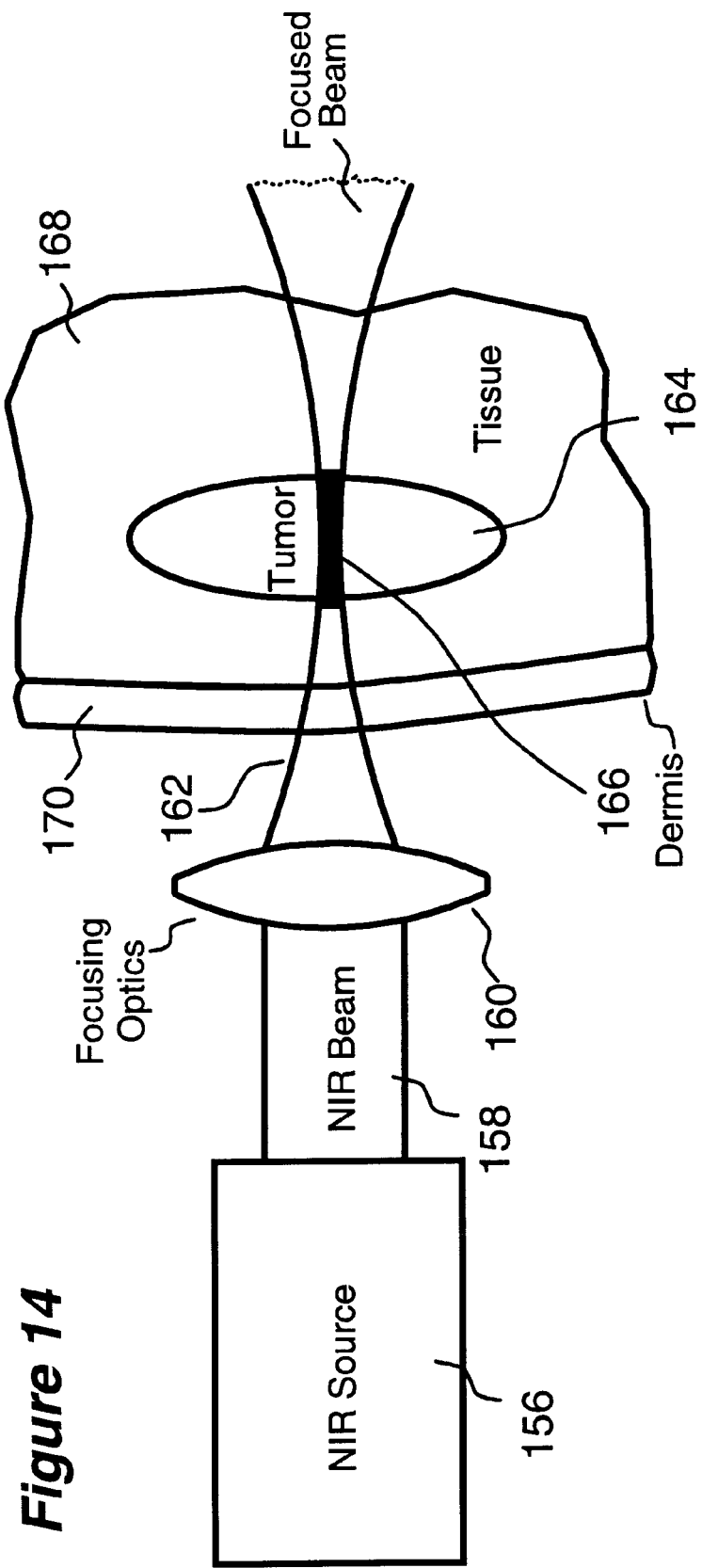
FIG. 14 shows the first preferred embodiment of the invention for selective two-photon NIR (near infrared) photo-activation of PDT agents.

Hence, it is a specific preferred embodiment of the subject invention to employ the output of a NIR source, such as the mode-locked titanium-sapphire laser, to induce simultaneous two-photon photo-activation of PDT agents using light at a wavelength approximately twice that necessary for conventional single-photon photo-activation. This preferred embodiment is shown in FIG. 14. The NIR Source 156 produces a beam of NIR radiation 158 consisting of a rapid series of high peak power pulses of NIR radiation. For example, standard commercially available mode-locked titanium-sapphire lasers are capable of outputting mode-locked pulses with durations <200 fs and pulse energies of about 20 nJ at pulse repetition frequencies in excess of 75 MHz; this source produces a quasi-continuous beam of light having a relatively low average power (up to several Watts) but high peak power (on the order of 100 kW) that is continuously tunable over a NIR wavelength band from approximately 690–1080 nm. The pulse train from the NIR source 156 constitutes a beam of NIR radiation 158 that is easily focussed using standard optical means, such as reflective or refractive optics 160. The focused NIR beam 162 can then be directed onto diseased tissue 164. Simultaneous two-photon photo-activation of the PDT agent will be substantially limited to the confocal region 166 of the focused beam 162 due to the high instantaneous irradiance level thatPDT agent is presat the focus. Furthermore, regardless of whether PDT agent is present in surrounding healthy tissue 168 or skin 170, insignificant collateral photo-activation or photodamage will occur outside the confocal region 166. This is a consequence of the non-linear relationship between instantaneous optical power and simultaneous two-photon excitation, which limits significant excitation to the confocal region 166; even if PDT agent is present outside of the confocal region 166, excitation power levels are below that necessary to produce significant photo-activation. This aspect of the preferred embodiment of the invention is in marked contrast with prior art, which afforded no practical means for tightly limiting the dimensions of the photo-activation zone along both the areal extent of the beam and its radial path. By scanning the location of the focus of the beam 162 throughout the volume of the diseased tissue 164, complete photo-activation of the PDT agent throughout the diseased tissue 164 can be effected. This scanning action can be produced by changing the position of the focus 162 relative to the diseased tissue 164, or by moving the diseased tissue 164 relative to a stationary focus 162 location. The quality of the confocal region 166 of the focused NIR beam 162 may be improved by pre-expanding the beam of NIR radiation 158, using a beam expander or other device, prior to focusing using standard optical means.

Figure 15:
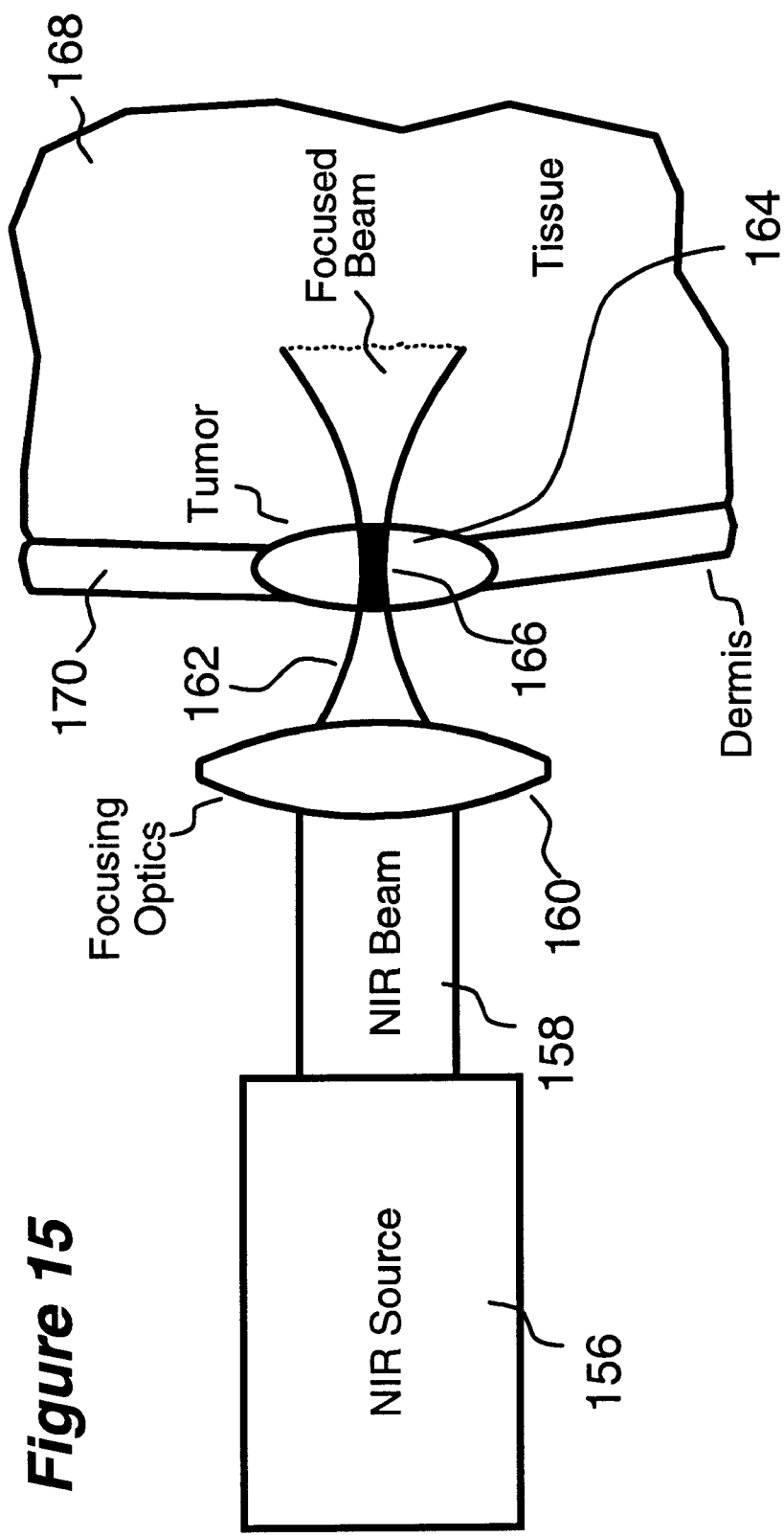
FIG. 15 shows a variation on the first preferred embodiment for topical photodynamic therapy using focused NIR light.
Figure 16:
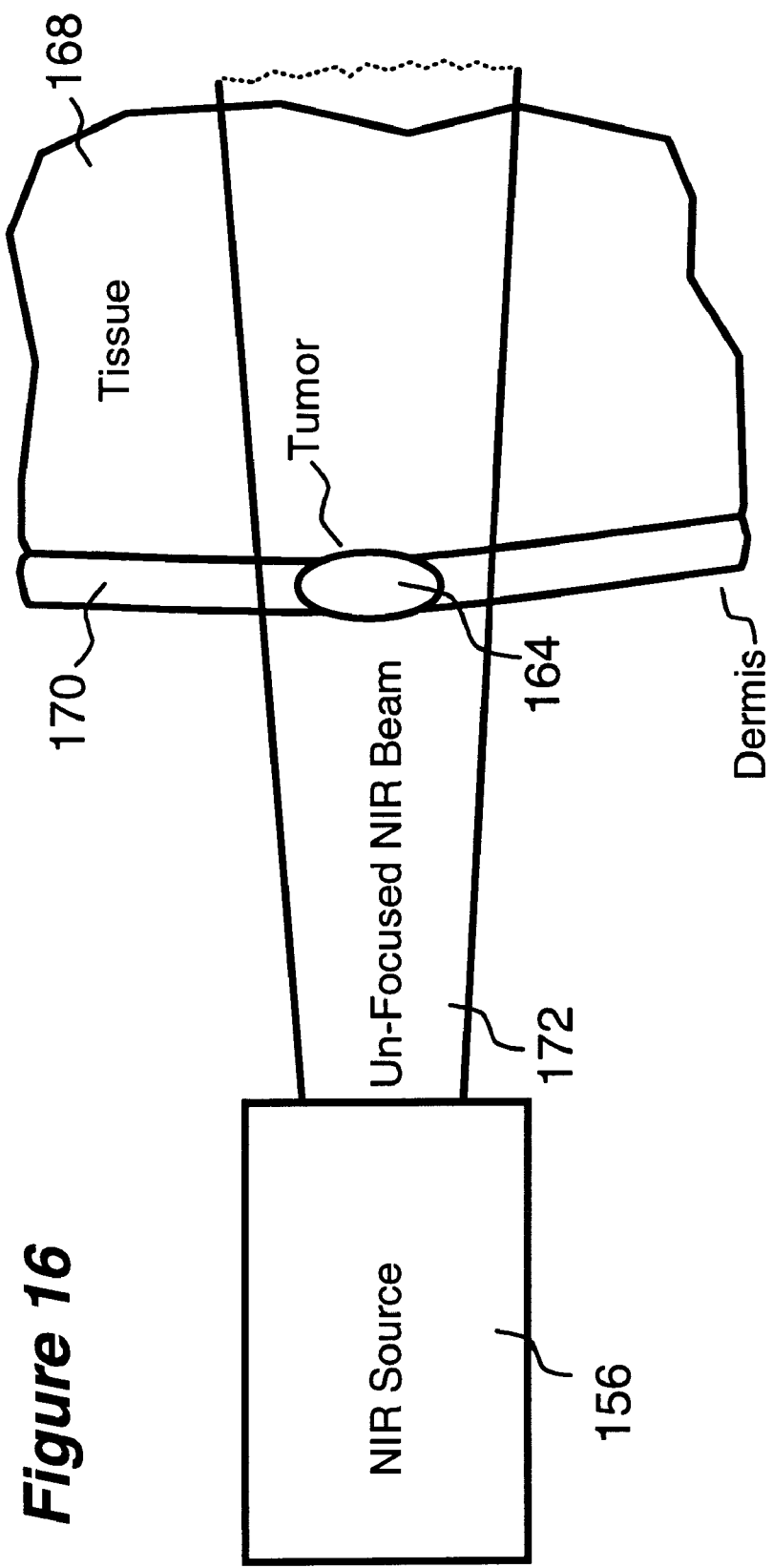
FIG. 16 shows a variation on the first preferred embodiment for topical photodynamic therapy using non-focused NIR light.

This simultaneous two-photon photo-activation embodiment has several variations for the treatment of topical diseased tissues, as shown in FIG. 15 and in FIG. 16. For example, the non-damaging nature of focused NIR light, shown in FIG. 15, or of non-focused NIR light, shown in FIG. 16, allows photo-activation of PDT agents at topical locations without risk to underlying or surrounding tissues.

Focused NIR simultaneous two-photon photo-activation of a PDT agent for topical therapy, as shown in FIG. 15, is effected when a beam of NMR radiation 158 from a NIR source 156 is focused 162 onto a diseased tissue 164 using standard optical means, such as reflective or refractive optics 160. In this manner, photo-activation of the PDT agent occurs only at the confocal region 166. The surrounding healthy tissue 168 and skin 170 are unaffected in this process, even if they also contain the PDT agent, since photo-activation is substantially limited to the confocal region 166. As described previously, a scanning action can be used to effect photo-activation of the PDT agent throughout the volume of the diseased tissue 164.

Non-focused NIR simultaneous two-photon photo-activation of a PDT agent for topical therapy, as shown in FIG. 16, is effected when an un-focused or expanded beam of light 172 from a NIR source 156 is directed onto a diseased tissue 164. This beam of light 172 may have a cross sectional area smaller than, equal to, or larger than that of the diseased tissue 164. If PDT agent is made to be substantially restricted to the volume of the diseased tissue 164, either through controlled application or by means of preferential systemic concentration, then therapeutic action will be substantially limited to the volume of the diseased tissue 164. Since the beam of light 172 is non-damaging to tissues that do not contain a significant concentration of PDT agent, damage to surrounding healthy tissue 168 and skin 170 is avoided. This embodiment may be particularly useful when the exact location, size and shape of the diseased tissue 164 are not known, or when it is otherwise undesirable to carefully control the location of application of the beam of light 172, since careful control of the location of the beam of light 172 is not critical for successful administration of this therapeutic regime. When non-focused light is used, employment of extremely high peak power excitation sources, such as Q-switched lasers or regeneratively amplified mode-locked lasers, may be beneficial due to their exceptionally high peak radiant power (which is in the GW range) that will thereby afford a high instantaneous irradiance over a large area.

Figure 17:
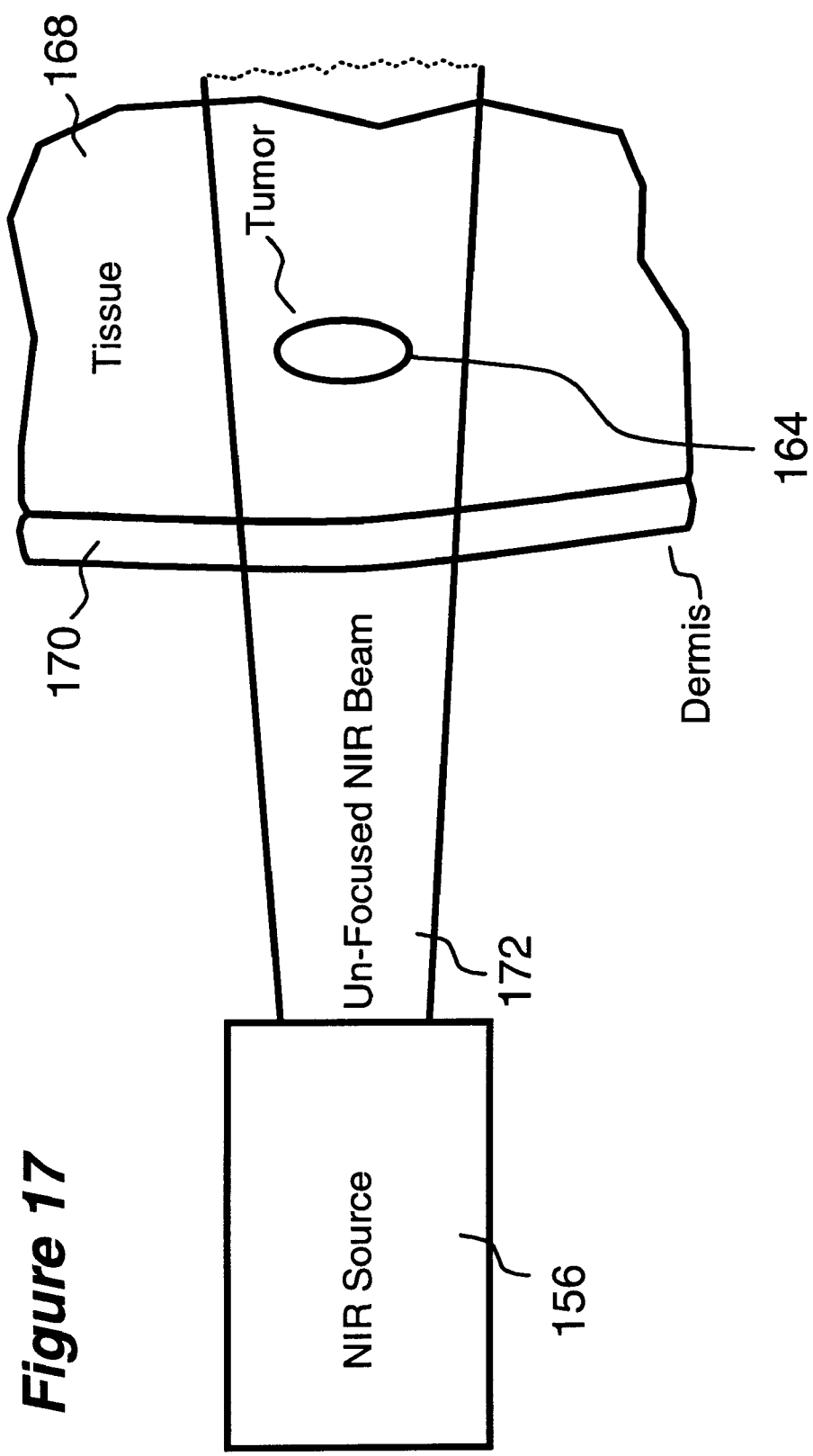
FIG. 17 shows a variation on the first preferred embodiment for photodynamic treatment of a subsurface lesion using non-focused NIR light.

A final related variation of this first preferred embodiment for simultaneous two-photon photo-activation is shown in FIG. 17, where an un-focused or expanded beam of light 172 from a NIR source 156 is directed onto a subsurface diseased tissue 164. This beam of light 172 may have a cross sectional area smaller than, equal to, or larger than that of the diseased tissue 164. If PDT agent is made to be substantially restricted to the volume of the diseased tissue 164, either through controlled application or by means of preferential systemic concentration, then therapeutic action will be substantially limited to the volume of the diseased tissue 164. Since the beam of light 172 is non-damaging to tissues that do not contain a significant concentration of PDT agent, damage to surrounding healthy tissue 168 and skin 170 is avoided. This embodiment may also be particularly useful when the exact location, size and shape of the diseased tissue 164 are not known, or when it is otherwise undesirable to carefully control the location of application of the beam of light 172, since careful control of the location of the beam of light 172 is not critical for successful administration of this therapeutic regime. As in the previous non-focused embodiment, employment of extremely high peak power excitation sources may be beneficial due to their exceptionally high peak radiant power and potential high instantaneous irradiance over a large area.

Figure 18:
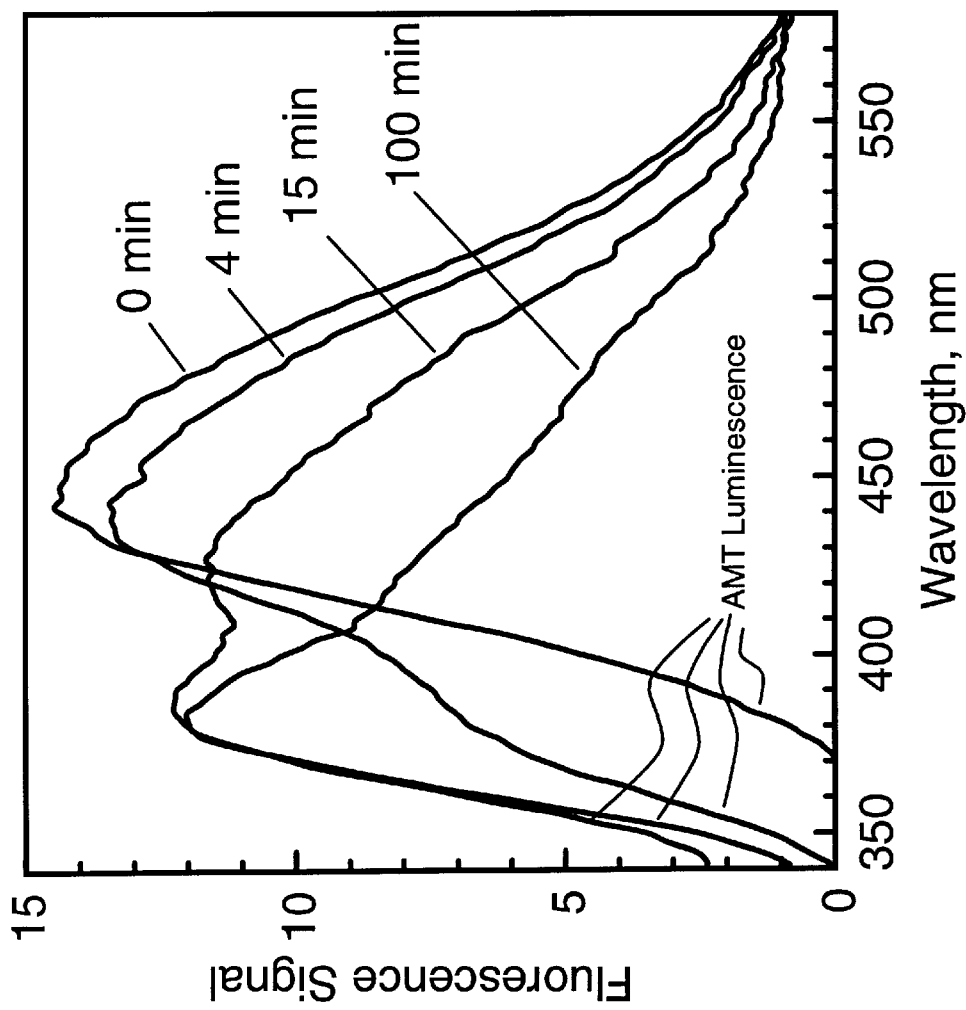
FIG. 18 shows the typical progressive shift in intercalated AMT (4'-aminomethyl-4,5',8-trimethylpsoralen) fluorescence band position for cumulative exposure to continuous UV radiation at 365 nm.
Figure 19:
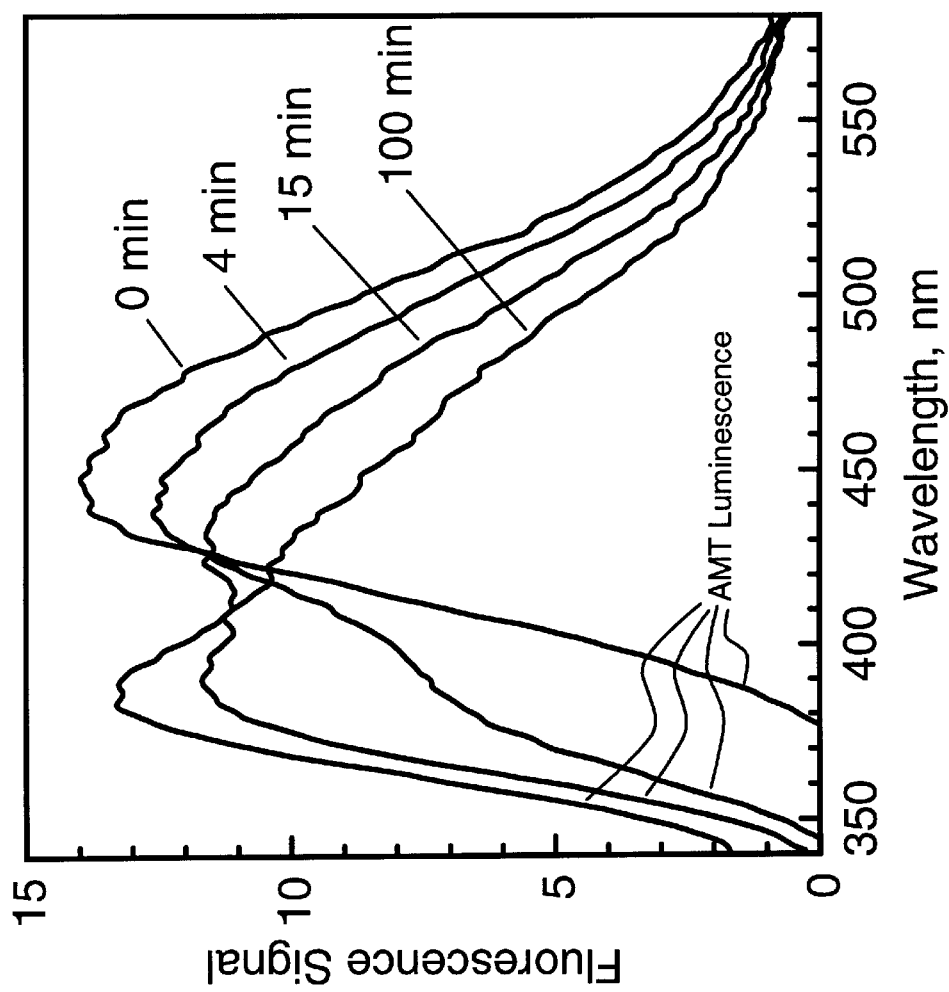
FIG. 19 shows the progressive shift in intercalated AMT fluorescence band position for cumulative exposure to sub-picosecond pulses of UV light at 364 nm.
Figure 20:
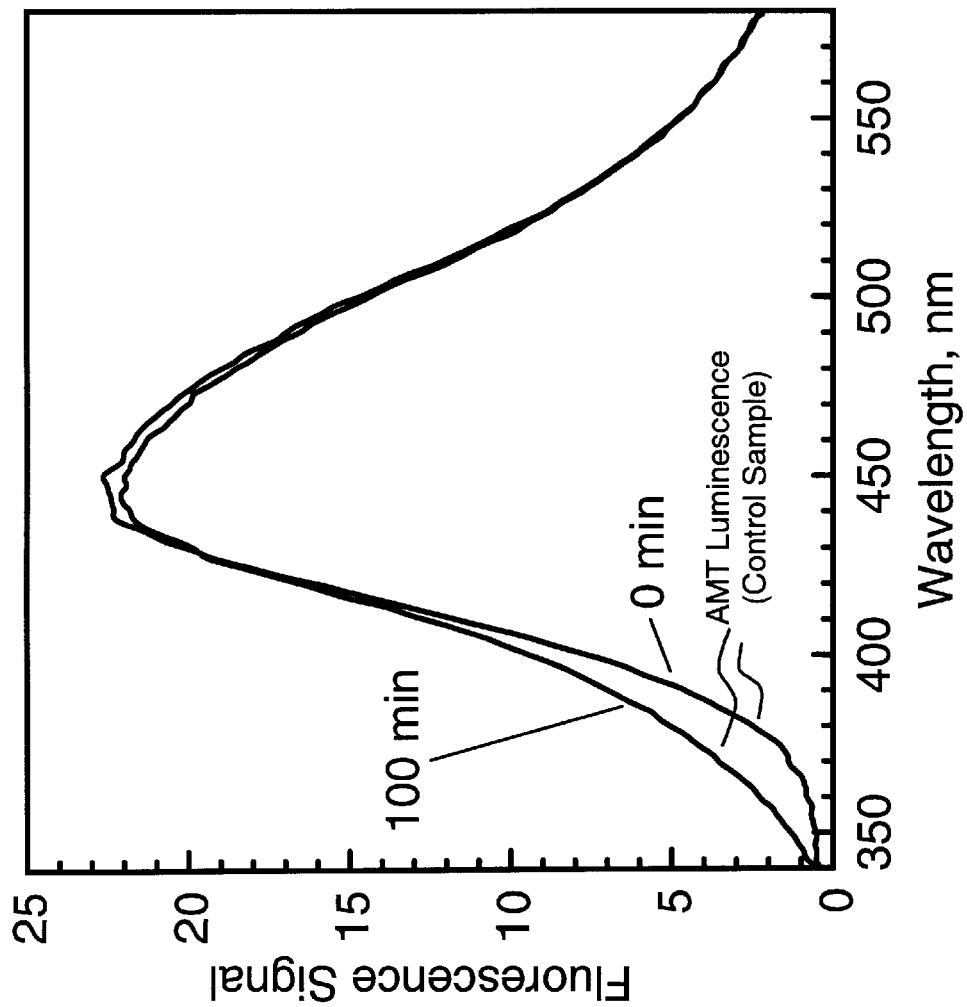
FIG. 20 shows control results for intercalated AMT upon exposure to fluorescent room light.
Figure 21:
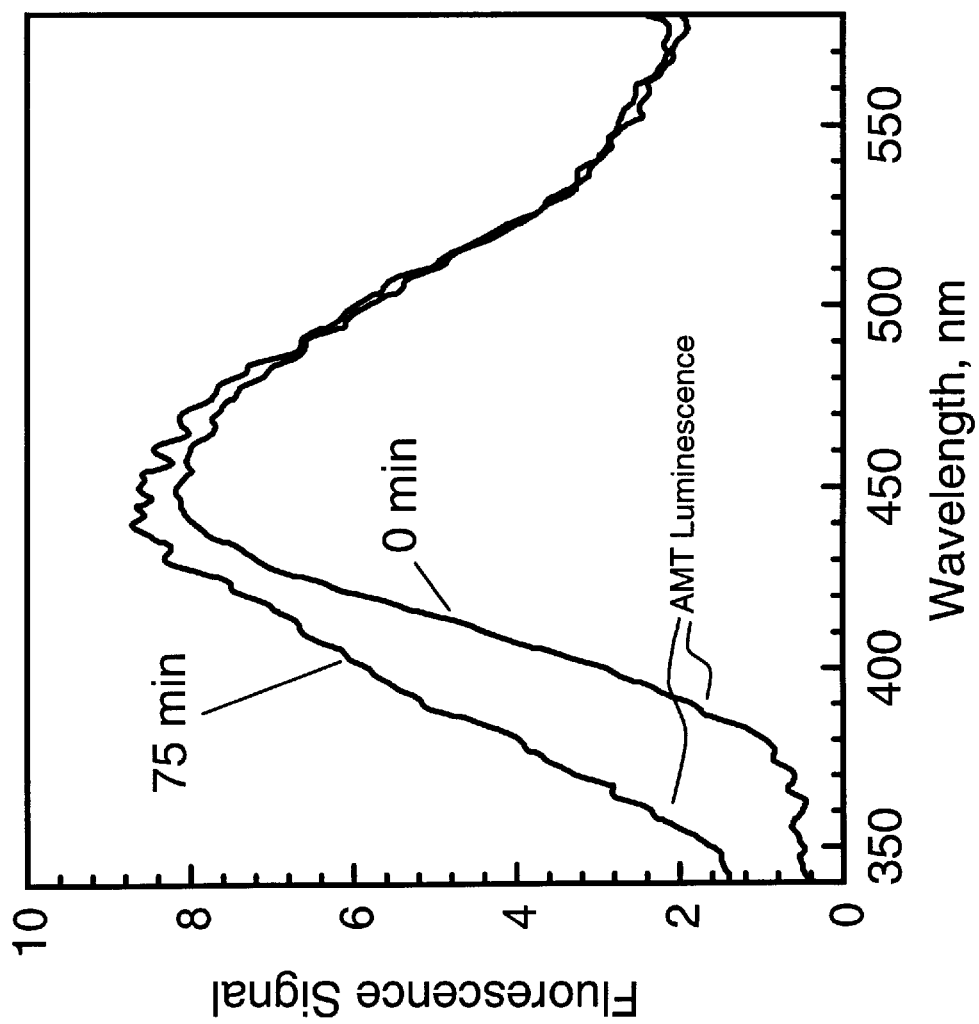
FIG. 21 shows the progressive shift in intercalated AMT fluorescence band position for cumulative exposure to sub-picosecond pulses of NIR light at 728 nm.

Comparison of Therapeutic Application of Single-photon and Simultaneous Two-photon Excitation The psoralen derivative AMF (4'-aminomethyl-4,5',8-trimethylpsoralen) is a known intercalating agent for the DNA double helix, and in the intercalated form undergoes stepwise adduct formation and cross-linking upon exposure to UV radiation. Adduct formation and cross-linking of intercalated psoralens is typically induced by single-photon exposure to light in the range of 320 to 400 nm. These reactions result in spectroscopic shifts in the luminescent properties of intercalated AMT upon adduct formation and cross-linking. Hence, adduct formation and cross-linking can be detected by measuring spectroscopic shifts in these luminescent properties. FIG. 18 shows the typical progressive shift in intercalated AMT fluorescence band position for various cumulative exposures to continuous UV radiation at 365 nm. Specifically, as adduct is formed upon UV exposure, the fluorescence band position for AMT shifts from 450 nm to 390 nm. If sub-picosecond pulses of UV light at 364 nm (produced by frequency doubling the 728 nm NIR output of a mode-locked titanium: sapphire laser) are used to irradiate a similar intercalated AMT sample, equivalent results are obtained, as shown in FIG. 19. The average photon flux for the data represented in FIG. 18 and FIG. 19 were made to be similar, thereby demonstrating that the AMT molecule is substantially insensitive to excitation pulse width, but rather is primarily responsive to cumulative photon dose. A control sample, shown in FIG. 20, confirms that intercalated AMT does not undergo significant adduct formation upon exposure to standard fluorescent room light. Irradiation of a similar intercalated AMT sample with sub-picosecond pulses of 728 nm NIR light (produced by a mode-locked titanium:sapphire laser) yields equivalent results to those obtained upon exposure to UV light, as shown in FIG. 21. Hence, equivalent stimulation of PDT action is shown for the model compound AMT using either direct single-photon excitation or simultaneous two-photon excitation.

Reports in the technical literature have suggested that relatively long excitation pulses may be needed to most efficiently stimulate complete activation of some PDT agents. Particularly in the case of sequential multi-step activation processes, such as adduct formation followed by cross-linking, it appears important that the optical energy necessary for successive steps be provided at appropriate intervals. For example, Hearst et al. (J. E. Hearst, T. T. Isaacs, D. Kane, H. Rapoport, and K. Straub, "The Reaction of the Psoralens with Deoxyribonucleic Acid. " Quarterly Review of Biophysics, 17 (1984) 1–44) use multi-pulse laser excitation methods with intercalated psoralen derivatives to show that the most efficient cross-linking occurs when optical energy is provided after an approximately 1 $\mu$s delay following initial stimulation of adduct formation. This has been attributed to the kinetic delays associated with slow conformational changes necessary between the adduct formation step and the cross-linking step. The quasi-continuous nature of the output of mode-locked lasers, such as the mode-locked titanium:sapphire laser, is well matched to this requirement, since such lasers typically emit a continuous train of pulses at 10–20 ns intervals; with this train of pulses an excited molecule has numerous opportunities to absorb the necessary energy required for subsequent photo-activation steps. However, an even more efficient match is provided by regeneratively amplified mode-locked lasers, such as the regeneratively amplified mode-locked titanium-:sapphire laser. In these lasers, short, extremely intense optical pulses can be emitted at 1–10 $\mu$s intervals; typically, this interval is adjustable over a large range of inter-pulse delays. Hence, the much higher peak powers attainable (in comparison with standard mode-locked lasers), coupled with the microsecond pulse repetition rates, make such sources ideal for exciting sequential multi-step simultaneous two-photon photo-activation processes.

Ames II Testing for Confirmation of Simultaneous Two-photon Excitation of PDT Agents The psoralen-derived PDT agent AMT (4'-aminomethyl-4,5',8-trimethylpsoralen) is known to produce therapeutic results through a combination of photo-activated adduct formation and cross-linking of DNA. Together, these reactions serve to slow or stop cellular reproduction and physiological processes in treated cells, such as tumor cells. Conventionally, AMT is photo-activated using single-photon excitation at UV wavelengths (ie, 365 nm); this produces mutations in DNA resulting from the formation of AMT adducts and cross-links with the DNA. Hence, to further evaluate the properties of simultaneous two-photon photo-activation for use as an improved means for photo-activation of PDT agents, Ames II mutagenicity assays were performed. Specifically, AMAX GTA-225 genotoxicity assays (from Xenometrix, Boulder, Colo.) were used to evaluate the mutagenicity of AMT in combination with two-photon activation at 730 nm.

The AMAX GTA-225 test assesses mutagenicity of an agent or process by detecting mutations in the histidine (His) operon in *Salmonella typhimurium*. This tester-strain of bacteria has been rendered histidine auxotrophic (His$^-$), due to specific point mutations in the His operon that make the bacteria incapable of producing histidine; such His$^-$ organisms cannot grow unless histidine is supplied to them. Thus, when subjected to a histidine-free environment, only those His⁻ auxotrophs which experience a reverse mutation (to become His⁺) can survive. Under non-cytotoxic conditions, application of a mutagen increases the number of tester-strain revertants above the spontaneous revertant baseline. Tester strains with both base-pair substitution (strains TA7001-TA7006) and frameshift (strain TA98) mutations were used for the AMAX GTA-225 assay. Tests were performed independently for the two types of tester strain using five conditions: (1) negative control (sterile water); (2) positive control; (3) optical radiation with sterile water, (4) AMT alone; and (5) AMT with optical radiation. The positive controls used for the base pair substitution and frameshift mutation were N-methyl-N'-nitro-N-nitrosoguanidine (MNNG, Sigma, 0.25 $\mu$M in the assay) and 2-nitrofluorene (2-NF, Aldrich, 0.5 $\mu$M in the assay), respectively. All conditions were tested in triplicate, and each of the individual 15 test cases were distributed to 48 microwells for prototrophic growth followed by assay scoring.

The optimal AMT concentration was determined independently for both type of tester strain. AMT was titrated into the particular tester-strain type followed by a 90-min. incubation in histidine-doped media at 37° C. with gentle agitation. Auxotrophic growth occurs during this incubation period for non-cytotoxic AMT concentrations. The AMT concentration used for the assay was chosen as the maximum non-cytotoxic dose, based on measurements of optical density at 600 nm following incubation. The AMT concentrations used for the base pair substitution and for the frameshift mutations were 720 $\mu$M and 390 $\mu$M, respectively, in the assay. To minimize the necessary irradiated volume, only the test chemicals (water, AMT or positive control) and the tester strain were mixed to obtain a total sample volume of 64 $\mu$L. Those samples undergoing subsequent irradiation were transferred to quartz microcuvettes; these samples were irradiated for 30 minutes, using a beam of 730-nm NIR laser radiation from a mode-locked titanium:sapphire laser that was focused along the longitudinal axis of the cuvette. When not being irradiated, each 64-$\mu$L sample was stored in a capped, UV-blocking vial, under ambient conditions.

Following initial exposure (to positive or negative control, AMT, light, or AMT with light), 440 $\mu$L of histidine-doped media was added to each 64-$\mu$L sample, and these were then incubated for 90-min. at 37° C. with gentle agitation. The dilute histidine concentration in this media allowed for finite auxotrophic cell division, and hence, expression of mutagenicity via His⁺ reversion. Following incubation, approximately 5× of histidine-free indicator medium was added to each sample; these were each subsequently distributed in 50-$\mu$L aliquots to 48 microwells. These microsamples were then incubated for approximately 40 hours at 37° C. without agitation. Because this second medium is void of histidine, this incubation step can support only prototrophic growth by His⁺ bacteria which developed as a consequence of reverse mutation during the initial incubation. Hence, prototrophic growth is an indication of mutagenicity. The indicator medium contained a pH indicator which was used to gauge the degree of prototrophic growth. The relative mutagenicity for a given test condition was assessed by scoring the number of positive microwells for each condition. Results for base-pair substitution and for frame-shift mutation are shown in Tables I and II.

TABLE I

Ames II test results for base-pair substitution mutation in *Salmonella typhimurium*, 35 hour incubation. AMT concentration, 720 $\mu$M; negative control, sterile distilled water; positive control, MNNG (N-methyl-N'-nitro-N-nitrosoguanidine, 0.25 $\mu$M in the assay).

| Test Condition | Test Results | | | |
|---|---|---|---|---|
| | Trial 1 | Trial 2 | Trial 3 | Ave ± $\sigma_n$ |
| Negative Control | 6 | 8 | 7 | 7.0 ± 0.6 |
| Two-Photon Stimulation | 13 | 9 | 17 | 13.0 ± 2.3 |
| AMT Treatment, No Light | 7 | 6 | 5 | 6.0 ± 0.6 |
| AMT Treatment + Two-Photon Stimulation | 0 | 0 | 0 | 0.0 ± 0.0 |
| Positive Control | 9 | 7 | 10 | 8.7 ± 0.9 |

TABLE II

Ames II test results for frame-shift mutation in *Salmonella typhimurium*, 40 hour incubation. AMT concentration, 390 $\mu$M; negative control, sterile distilled water; positive control, 2-NF (2-nitrofluorene, 0.5 $\mu$M in the assay).

| Test Condition | Test Results | | | |
|---|---|---|---|---|
| | Trial 1 | Trial 2 | Trial 3 | Ave ± $\sigma_n$ |
| Negative Control | 3 | 5 | 2 | 3.3 ± 0.9 |
| Two-Photon Stimulation | 3 | 4 | 3 | 3.3 ± 0.3 |
| AMT Treatment, No Light | 9 | 2 | 4 | 5.0 ± 2.1 |
| AMT Treatment + Two-Photon Stimulation | 0 | 0 | 2 | 0.7 ± 0.7 |
| Positive Control | 42 | 45 | 44 | 43.7 ± 0.9 |

The results in Tables I and II show that AMT treatment alone and two-photon stimulation in the absence of a photo-activation agent (such as AMT) have no significant effect on the test bacteria. In contrast, the very low prototrophic growth scoring for AMT treatment with two-photon stimulation would seem to indicate little or no mutation for both the base-pair mutation and frame shift mutation tests. However, when these samples were subsequently incubated in a histidine enriched media they showed no growth. Thus, these tests show that the AMT treatment with simultaneous two-photon stimulation not only causes mutations in the test bacteria but in fact also completely kills them. This demonstrates efficacy of PDT therapy using simultaneous two-photon excitation, since such excitation not only produces the necessary agent activation requisite for therapeutic effect, but is also capable of killing the cells undergoing treatment. Furthermore, the low mutagenicity observed for two-photon stimulation alone demonstrates that this photo-activation method is non-damaging to cells in the absence of a photo-activating substance.

Implication of the Simultaneous Two-photon Activation Method for Standard PDT Agents and for New PDT Agents Standard PDT agents have tissue specificities that in general are based on the combined chemical and physical properties of the agent and the tissue, such as a cancerous lesion. For example, psoralen and its derivatives (including 5-methoxypsoralen [or 5-MOP]; 8-methoxypsoralen [8-MOP]; 4,5',8-trimethylpsoralen [TMP]; 4'-aminomethyl-4,5',8-trimethylpsoralen [AMT]; 4'-hydroxymethyl-4,5',8-trimethylpsoralen [HMT]; 5-chloromethyl-8-methoxypsoralen, Angelicin [isopsoralen]; 5-methlyangelicin [5-MIP]; and 3-carbethoxypsoralen);

various porphyrin and hematoporphyrin derivatives (including haematoporphyrin derivative [HPD];

Photofrin II; benzoporphyrin derivative [BPD]; protoporphyrin IX [Pp IX]; dye hematoporphyrin ether [DHE]; polyhematoporphyrin esters [PHE]; 13,17-N,N,N-dimethylethylethanolamine ester of protoporphyrin [PH1008]; tetra(3-hydroxyphenyl)porphyrin [3-THPP]; tetraphenylporphyrin monosulfonate [TPPS1]; tetraphenylporphyrin disulfonate [TPPS2a]; dihematoporphyrin ether; meso-tetraphenyl-porphyrin; and mesotetra(4N-methylpyridyl)porphyrin [T4MPyP]) along with various tetraazaporphyrins (including, octa-(4-tert-butylphenyl)-tetrapyrazinoporphyrazine [OPTP]; tetra-(4-tert-butyl) phthalocyanine [$t_4$-PcH$_2$]; and tetra-(4-tert-butyl) phthalocyanatomnagnesium [$t_4$-PcMg]);

various phthalocyanine derivatives (including chloroalurninum-sulfonated phthalocyanine [CASPc]; chioroaluminum phthalocyanine tetrasulfate [AlPcTS]; mono-, di-, tri- and tetra-sulphonated aluminum phthalocyanines [including AlSPc, AlS2Pc, AlS3Pc and AlS4Pc]; silicon phthalocyanine [SiPcIV]; zinc(II) phthalocyanine [ZnPc]; bis(di-isobutyl octadecylsiloxy)silicon 2,3-naphthalocyanine [isoBOSINC]); and Ge(IV)-octabutoxy-phthalocyanine various rhodamine derviatives (including rhodamine-101 [Rh-101]; rhodamine-110[Rh-110]; rhodamine-123 [Rh-123]; rhodamine-19[Rh-19]; rhodamine-560[Rh-560]; rhodamne-575[Rh-575]; rhodamine-590[Rh-590]; rhodamine-610[Rh-610]; rhodamine-640[Rh-640]; rhodamine-6G [Rh-6G]; rhodamine-700[Rh-700]; rhodamine-800[Rh-800]; rhodamiine-B[Rh-B]; sulforhodamne 640 or 101; and sulforhodamine B);

various coumarin derivatives (including coumarin 1, 2, 4, 6, 6H, 7, 30, 47, 102, 106, 120, 151, 152, 152A, 153, 311, 307, 314, 334, 337, 343, 440, 450, 456, 460, 461, 466, 478, 480, 481, 485, 490, 500, 503, 504, 510, 515, 519, 521, 522, 523, 535, 540, 540A, 548);

various benzophenoxazine derivatives (including 5-ethylamino-9-diethylaminobenzo[a]-phenoxazinium [EtNBA]; 5-ethylamino-9-diethylaminobenzo[a] phenothiazinium [EtNBS]; and 5-ethylamino-9-diethylaminobenzo[a]phenoselenazinium [ENBSe]);

chlorpromazine and its derivatives;

various chlorophyll and bacteriochlorophyll derivatives (including bacteriochlorin a [BCA]);

various metal-ligand complexes, such as tris(2,2'-bipyridine)ruthenium (II) dichloride (RuBPY);

pheophorbide a [Pheoa]; merocyanine 540[MC540]; Vitamin D; 5-amino-laevulinic acid [ALA]; photosan; chlorin e6, chlorin e6 ethylenediamide, and mono-L-aspartyl chlorin e6; pheophorbide-a [Ph-a]; phenoxazine Nile blue derivatives (including various phenoxazine dyes);

various charge transfer and rediative transfer agents, such as stilbene, stilbene derivatives and 4-(N-(2-hydroxyethyl)-N-methyl)-aminophenyl)-4'-(6-hydroxyhexylsuffonyl)stilbene (APSS); and numerous other photo-active or photo-sensitizing agents, will in general become accumulated either at or near a point of application or semi-selectively within a specific tissue due to differences in the physilead r chemical properties of the tissue which lead to partitioning of the PDT agent into the tissue. Furthermore, these PDT agents are conventionally activated using single-photon or sequential two-photon activation that promotes one or more photo-chemical or photo-physical processes, including but not limited to bond formation or cleavage, adduct formation, cross-inking, free radical production, singlet oxygen production, generation of toxic substances, and energy transfer. The conventional methods of activation afford minimal selectivity in the extent or depth of activation. and are normally limited to use with superficial tissues or lesions. The mechanism responsible for induction of PDT action may be direct activation of a single agent (such as stimulation of adduct formation upon optical excitation of AMT), or indirect photo-activation (for example, photo-activation of an optical absorber, such as APSS, which subsequently transfers energy to a proximal bioactive agent, such as Photofrin). However, it is clear from the foregoing first preferred embodiment and supporting performance and efficacy data that the invention taught in this application is applicable to all of these listed PDT agents and photosensitizers as well as other PDT agents and photosensitizers not specifically listed. Specifically, all of these agents will be responsive to simultaneous two-photon excitation at wavelengths approximately twice those used for single-photon excitation, and once excited, will exhibit behaviors equivalent to those resulting from single-photon excitation. Specifically, the results shown in this application for various examples of the photophysical and photochemical equivalency in excited state behavior for single-photon excitation and for simultaneous two-photon excitation (for example in the case of RuBPY photochemistry, for AMT adduct formation with DNA, and for Ames II assay effects on DNA and cell viability) demonstrate that simultaneous two-photon excitation is applicable for successful activation of all PDT agents and agent activation mechanisms. Furthermore, the improvements over control of point of application and in reduction of collateral damage afford additional specific advantages to the use of simultaneous two-photon excitation in place of conventional single-photon or sequential two-photon activation. These include enhanced depth of penetration, enhanced spatial control over point of application, and reduced side-effects from PDT treatment.

Many new PDT agents are being developed that are susceptible to direct single-photon activation in the NIR; the intention with these agents is reduction of side-effects and other limitations associated with conventional UV or visible photo-activation. An example is Photofrin II and related agents that can be photo-activated using single-photon excitation at wavelengths greater than 500 nm. The invention taught in this application has specific advantages with these classes of PDT agent as well. Specifically, use of simultaneous two-photon activation at wavelengths in the 1.0 to 2.0 $\mu$m spectral band can afford considerably higher depth of penetration than that possible with single-photon activation because of greatly reduced tissue absorptance and scatter in this band in comparison to the 0.5 to 1.0 $\mu$m band; also, the spatial localization advantages of simultaneous two-photon activation taught herein will afford improved control over the point of application of such therapy in comparison with single-photon activation methods. NIR laser sources such as mode-locked optical parametric oscillators and other such devices can be readily employed to provide optical energies suitable for activation of the NIR PDT agents using simultaneous two-photon methods.

Implication of the Simultaneous Two-photon Activation Method for Advanced Biogenic PDT Agents Under ideal conditions, standard PDT agents derive target specificity based on chemical or physical affinity for diseased tissue. In this way, PDT agents partition into or otherwise become concentrated on or in diseased tissue.

Unfortunately, this target specificity is usually not perfect. In fact, it would be desirable to have an improved method for increasing specificity in the targeting of PDT agent destination and activation. A means for achieving such improvement in specificity of PDT agent destination is based on utilization of specific biological signatures of disease. Specifically, by coupling anti-sense oli gonucleotide agents to one or more photo-active moieties, such as psoralen or its derivatives, new biogenic PDT agents are created that are capable of selectively attacking only diseased cells. Moreover, the basic approach is easily extended to numerous genetic-based diseases or disorders by changina the oligomeric code used for the biogenic probe. Employment of simultaneous two-photon activation enables this powerful approach to be applied using the combined bio-specificity of the biogenic probe and the high spatial localization inlhrent to the simultaneous two-photon photo-activation process. Thus, the action of a new PDT therapeutic regime based on combined genetic and photonic specificity can be made to be very specifically targeted to a particular organ, tissue, or lesion.

Figure 22:
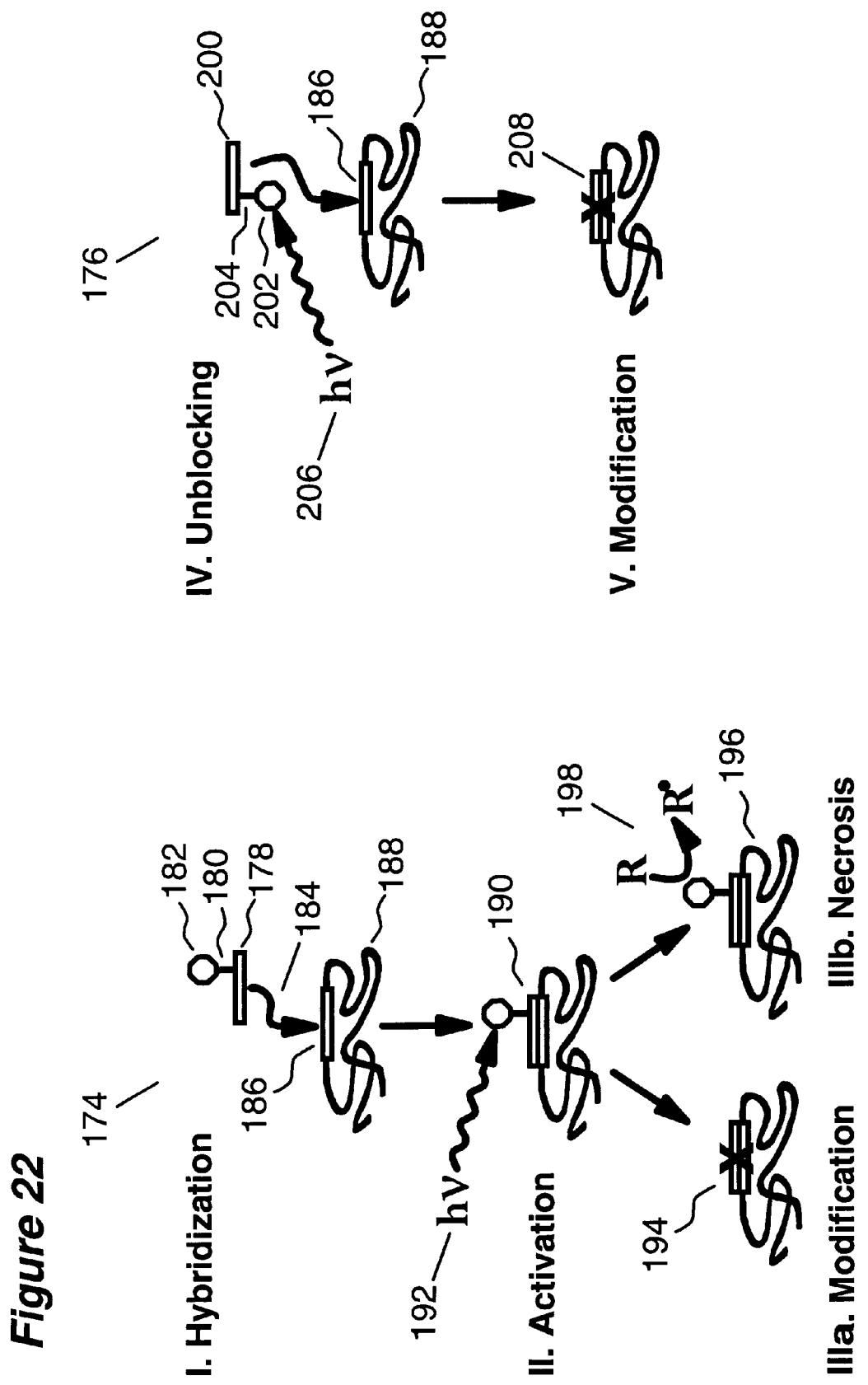
FIG. 22 shows intra-cellular photo-activation of a genetic PDT agents.

As an example, a biogenic probe can be "chemically tagged" with a photo-active group designed to undergo efficient simultaneous two-photon activation, such as fluorescein isothiocyanate (or FITC). A DNA sequence complementary (anti-sense) to the human p53 tumor suppressor gene has been used as a model, as shown in FIG. 22. This gene was chosen since it plays a predominant role in the development of breast cancer in humans and mice. A majority of breast tumors in humans develop due to a deletion or mutation in this critical growth suppressing gene. Since alterations in p53 occur well before the developmentof tumors, a therapy based on changes in this gene can be used to destroy precancerous cells prior to tumor development. Alterations in differentiation and growth-promoting genes (oncogenes) are also critical to the initiation and progression of tumor virulence. Suppression of growth-promoting activity via anti-sense DNA therapy is known to be a potential treatment for cancer. However, uncontrolled anti-sense suppression of these genes is highly toxic in normal cells. Secondary control over the site of activation of anti-oncogene probes using precisely targeted two-photon photo-activation makes this approach feasible for in vivo treatment of cancer.

FIG. 22 shows that intra-cellular photo-activation of the biogenic PDT agent can be made to occur following hybridization 174 or unblocking 176. Specifically, for biogenic PDT agent activation following hybridization 174, an anti-sense genetic probe 178 coupled via a coupling means 180 to a photo-active agent 182 is made to hybridize 184 with a target genetic sequence 186 contained in DNA or RNA 188. Delivery of the probe prior to hybridization is effected using transfection methods or other means to introduce the biogenic PDT probe into a cell. The hybridized probe 190 will not affect behavior of the cell or affect genetic transcription or other cellular processes until it is photo-activated. Activation is effected upon irradiation of the hybridized probe 190 with optical energy 192. Photo-activation of the hybridized probe 190 upon irradiation with optical energy 192 can produce subsequent modification 194 of cellular genetic material, including cross-linking, cutting, and base substitution, which affects cellular function, reproduction, or viability. Alternatively, photo-activation of the hybridized probe 190 upon irradiation with optical energy 192 can produce cell necrosis 196 through the initiation of toxic reactions or generation of toxic materials 198, including free-radical compounds and singlet oxygen. PDT agent activation following unblocking 176 is achieved when an anti-sense genetic probe 200 that is blocked by the presence of a photo-active agent 202 coupled to the anti-sense genetic probe 200 via a coupling means 204 is unblocked upon photo-activation of the photo-active agent 202 with optical energy 206. Note that prior to unblocking 176 the blocked anti-sense genetic probe 200 is incapable of hybridizing or otherwise interacting with its target genetic sequence 186. This may be due to steric hindrance, changes in polarity, tertiary or quaternary confirmation, or other effects resulting from the presence of the photo-active agent 202. Upon unblocking, the anti-sense genetic probe 200 is free to hybridize 208 or otherwise interact with the target genetic sequence 186, leading to change in cellular function, reproduction, or viability.

The example shown in FIG. 22 uses procaryotic or eukaryotic cellular genetic material as an example. However, it will be clear that the invention taught herein is not limited to cellular genetic material, but can be made to apply to genetic materials composing or derived from viruses or other sources. It will be equally clear that targeting methods based on immunological or other bio-specific means rather than genetic means may be substituted without loss of efficacy of the invention. Specifically, agent specificity based on antigen-antibody methods, where an antibody probe is coupled to a photo-active group, provides a powerful new means for treatment of disease and infection. Additional means for achieving biospecificity in agent targeting include but are not limited to use of ligands, haptens, carbohydrate, lipid, or protein receptors or complexing agents, chelators, and encapsulating vehicles, such as liposomes, fullerenes, crown ethers, and cyclodextrins. Regardless of the mechanism responsible for targeting of the probe agent, use of simultaneous two-photon activation of the probe agent allows the site of application to be further regulated based on the inherent precision possible over control of the site of non-linear photo-activation. This secondary level of control via spatially-specific photo-activation is very important for many biogenic based therapies due to their potential toxicity in normal cells. Hence, employment of simultaneous two-photon activation is critical in enabling such therapies to be used successfully.

Second Exemplary Embodiment of the Invention

Figure 23:
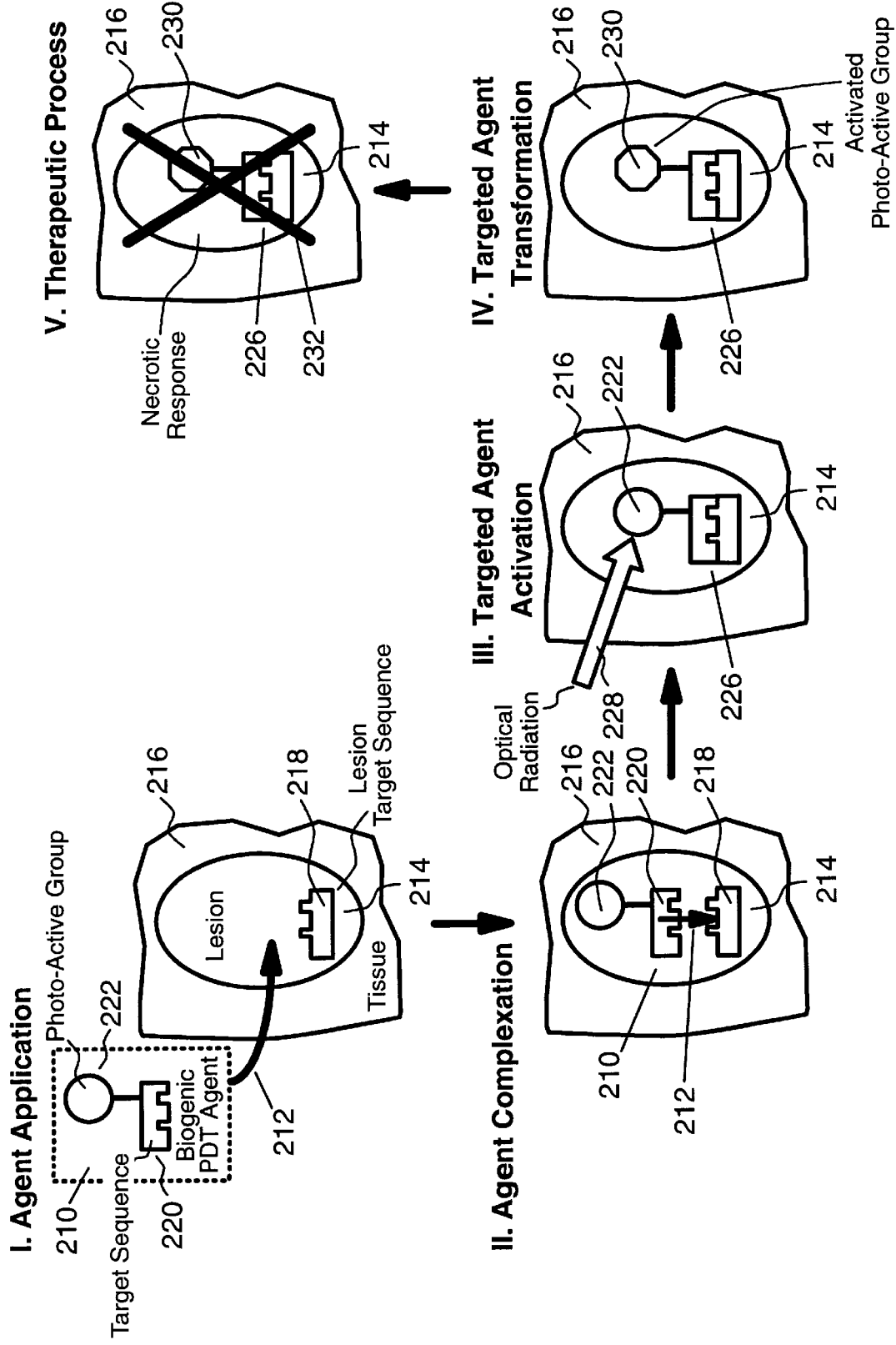
FIG. 23 shows the second preferred embodiment of the invention for employment of biogenic PDT agents.

Hence, it is a specific preferred embodiment of the present subject invention to employ biogenic PDT agents to improve target specificity and effectiveness in the administration of PDT, particularly when such agents are used in conjunction with the unique properties of two-photon photo-activation. This preferred embodiment is shown in FIG. 23. A biogenic PDT agent 210 is applied 212 topically onto or systemically into a lesion 214, such as a cancerous growth or microbial infection; this lesion 214 may be located on or within otherwise healthy tissue 216. The biogenic PDT agent 210 achieves specificity for the lesion 214 based on a lesion biological target sequence 218 that is substantially unique to the lesion 214 and that is complementary to an agent biological target sequence 220. This agent biological target sequence 220 is attached to a photo-active group 222. Complexation 224 of the agent biological target sequence 220 with the lesion biological target sequence 218 produces a targeted agent 226 that is substantially localized at the site of the lesion 214. The photo-active group 222 of the targeted agent 226 is subsequently transformed through means of interaction with optical radiation 228 into an activated photo-active group 230; this transformation results from stimulation of a photo-chemical or photo-physical transformation process in the photo-active group 222 by the incident optical radiation 228. Transformation of the photo-active group 222 into an activated photo-active group 230 results in localized cell necrosis or other desirable therapeutic process 232. This transformation of the photo-active group 222 may be spatially localized through application of a two-photon activation process arising from illumination of the photo-active group 222 with a focused or non-focused beam of light emanating from a high-irradiance optical source, such as a mode-locked titanium:sapphire laser. In this way, the site of application of the therapeutic process 232 may be controlled by a combination of specificities provided by the agent biological target sequence 220 and by controlling the site of application of incident optical radiation 228.

Diseases like cancer and inherited genetic defects could be selectively remedied by a therapy based on biogenic PDT, specifically since the approach is inherently capable of non-invasively modifying genetic material. A targeted, non-invasive method to specifically damage or modify aberrant growth genes would greatly improve the efficacy of cancer treatment while localizing the treatment to cancer cells alone. Indeed, aberrant expression of any genetic element in a particular tissue caused by an inherited or spontaneous genetic event could be treated using this method. Applicability extends to treatment of infectious diseases, particularly but not limited to those caused by retroviral infectious agents, including AIDS, and to microbial infections, such as localized or systemic bacterial infections.

Special chromophoric photo-active groups can be chosen or designed that offer improved cross-section and high efficiency for selective transformation (such as bond cleavage or free-radical formation) upon simultaneous two-photon excitation. Such molecules could be used alone as advanced PDT agents, or incorporated into biogenic PDT agents. For example, specific gene sequences might be destroyed, modified, or their expression level changed in vivo through the use of such an agent that selectively binds with a target sequence and then is activated using optical radiation.

It will be clear that while the foregoing disclosure has focused on example therapeutic applications using simultaneous two-photon excitation of PDT agents with pulsed NIR optical radiation produced by mode-locked titanium:sapphire lasers, the invention is not limited to such two-photon excitation nor to such narrowly defined optical sources. In fact, aspects of the invention are applicable when optical excitation is effected using linear or other non-linear methods. For example, the biogenic PDT agents described herein are also responsive to linear optical excitation processes. Also, various other optical sources are applicable, alone or in combination, such as continuous wave and pulsed lamps, diode light sources, semiconductor lasers; other types of gas, dye, and solid-state continuous, pulsed, or mode-locked lasers, including: argon ion lasers; krypton ion lasers; helium-neon lasers; helium-cadmium lasers; ruby lasers; Nd:YAG, Nd:YLF, Nd:YAP, Nd:YVC4, Nd:Glass, and Nd:CrGsGG lasers; regeneratively amplified lasers; Cr:LiSF lasers; Er:YAG lasers; F-center lasers; Ho:YAF and Ho:YLF lasers; copper vapor lasers; nitrogen lasers; optical parametric oscillators, amplifiers and generators; and sunlight.

Further, while the foregoing disclosure has focused on therapeutic applications for in vivo treatment of disease, it will also be clear that the invention has additional utility whenever selective modification of a tagged agent or an otherwise responsive target agent is desirable. Specifically, application of the invention in the control of manufacture or purification of materials of biological origin or contaminated with materials of biological origin are covered within the scope of this invention. As an example, selective treatment or purification of biological fluids, such as blood or plasma, based on the targeted interaction of a photo-sensitizable agent with a target entity, such as the HIV virus, is anticipated. This approach could serve a therapeutic role in the treatment of HIV infection and as a protective measure for the prevention of transmission of HIV through blood transfusions. As a second example, manufacture of extremely pure biological products, such as cell cultures, wherein a heterogeneous parent culture is purified by destruction of a targeted contaminant agent, is anticipated. As a third example, production of genetically induced biological products based on selective stimulation of one or more specific gene sequences in targeted biological agents is anticipated.

In addition to various biological applications, it will further be clear that numerous non-biological applications will be made possible or their efficiencies dramatically improved by utilization of the subject invention, including the manufacture of high purity or commodity materials, especially where the special properties of non-linear optical excitation are important. For example, production or processing of specialty chiral chemicals, pigments, paints, polymeric materials and other industrial or commercial agents can be improved through application of aspects of the subject invention. Specifically, the unique selection rules, selectivity advantages, and localization of activation, offer advantages in many materials production or processing steps. In fact, these examples make it clear that the subject invention actually constitutes a general materials processing paradigm, wherein the special properties of non-linear optical excitation are used on biological or non-biological materials to effect specific improvements in the selective conversion of starting materials into products, regardless of whether the transformation is from tumor to necrotic tissue or from one molecular agent to another.

Also, it is clear that in certain cases the unique properties of non-linear optical excitation will be useful, even without the addition of specific responsive agents to a system. For example, the localized application of non-linear optical radiation at visible or NIR wavelengths may be useful for stimulation of localized processes that are in many ways comparable to those normally achieved through direct treatment with UV wavelengths. As an example, treatment of superficial or subsurface cancerous lesions is anticipated using visible or NIR non-linear excitation to initiate localized necrosis that is equivalent to but more effectively localized than that possible with linear UV excitation. Similar extension of the method to other optical bands is also expected, for example whereby 10 $\mu$m light is used to effect highly localized ablation of lesions of the eye or skin.

Also, while the foregoing example has focused primarily on therapeutic issues pertaining to humans, direct applicability to microbial, plant and animal specimens will also be obvious. For example, treatment of disease in livestock, breeding stock, or in other veterinary capacities is envisioned. Also, use of the method for treatment or as a means for achieving selectivity in microbial or cell cultures is envisioned. For example, portions of the subject invention will be useful for purification of heterogeneous cell cultures and in the expression of cell function in vitro. Hence, the invention has application to the fields of genetic engineering, animal husbandry, reproductive therapy, cloning, and many others.

It will be understood that each of the elements described above, or two or more together, may also find useful application in other types of constructions or applications differing from the types described above.

While the invention has been illustrated and described as embodied in a general method for improved selectivity in photo-activation of therapeutic agents, it is not intended to be limited to the details shown, since it will be understood that various omissions, modifications, substitutions and changes in the forms and details of the method illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A method for producing at least one photo-activated molecular agent in a particular volume of a material, the method comprising treating the particular volume of the material with light sufficient to promote a simultaneous two-photon excitation of at least one photo-active molecular agent contained in the particular volume of the material, wherein the at least one photo-active molecular agent becomes a photo-activated molecular agent in the particular volume of the material.

2. The method of claim 1 wherein the material is selected from the group consisting of plant tissue and animal tissue.

3. The method of claim 1 wherein the light sufficient to promote a simultaneous two-photon excitation of the photo-active molecular agent is laser light.

4. The method of claim 3 wherein the laser light is pulsed laser light.

5. The method of claim 1 wherein the light sufficient to promote a simultaneous two-photon excitation of the photo-active molecular agent is a focused beam of light.

6. The method of claim 5 wherein the focused beam of light is laser light.

7. The method of claim 6 wherein the laser light is pulsed laser light.

8. The method of claim 1 wherein the material is pre-treated with at least one photo-active molecular agent such that the material retains at least a portion of the at least one photo-active agent at the time that the particular volume of the material is treated with light sufficient to promote a simultaneous two-photon excitation of at least one of the at least one photo-active molecular agent.

9. The method of claim 8 wherein the at least one photo-active molecular agent is selected from the group consisting of psoralen, 5-methoxypsoralen (5-MOP), 8-methoxypsoralen (8-MOP), 4,5',8-trimethylpsoralen (TMP), 4'-aminomethyl-4,5',8-trimethylpsoralen (AMT), 5-chloromethyl-8-methoxypsoralen (HMT), angelicin (isopsoralen), 5-methylangelicin (5-MIP), 3-carboxypsoralen, porphyrin, haematoporphyrin derivative (HPD), photofrin II, benzoporphyrin derivative (BPD), protoporphyrin IX (PpIX), dye haematoporphyrin ether (DHE), polyhaematoporphyrin esters (PHE), 13,17-N,N,N-dimethylethylethanolamine ester of protoporphyrin (PH1008), tetra(3-hydroxyphenyl)-porphyrin (3-THPP), tetraphenylporphyrin monosulfonate (TPPS1), tetraphenylporphyrin disulfonate (TPPS2a), dihaematoporphyrin ether, mesotetraphenylporphyrin, mesotetra(4N-methylpyridyl) porphyrin (T4MpyP), octa-(4-tert-butylphenyl) tetrapyrazinoporphyrazine (OPTP), phthalocyanine, tetra-(4-tert-butyl)phthalocyanine ($t_4$-PcH$_2$), tetra-(4-tert-butyl) phthalocyanatomagnesium ($t_4$-PcMg), chloroaluminum sulfonated phthalocyanine (CASPc), chloroaluminum phthalocyanine tetrasulfate (AlPcTS), mono-sulfonated aluminum phthalocyanine (AlSPc), di-sulfonated aluminum phthalocyanine (AlS2Pc), tri-sulfonated aluminum phthalocyanine (AlS3Pc), tetra-sulfonated aluminum phthalocyanine (AlS4Pc), silicon phthalocyanine (SiPc IV), zinc II phthalocyanine (ZnPc), bis(di-isobutyl octadecylsiloxy) silicon 2,3-naphthalocyanine (isoBOSINC), germanium IV octabutoxyphthalocyanine (GePc), rhodamine 101 (Rh-101), rhodamine 110 (Rh-110), rhodamine 123 (Rh-123), rhodamine 19 (Rh-19), rhodamine 560 (Rh-560), rhodamine 575 (Rh-575), rhodamine 590 (Rh-590), rhodamine 610 (Rh-610), rhodamine 640 (Rh-640), rhodamine 6G (Rh-6G), rhodamine 700 (Rh-700), rhodamine 800 (Rh-800), rhodamine B (Rh-B), sulforhodamine 101, sulforhodamine 640, sulforhodamine B, coumarin 1, coumarin 2, coumarin 4, coumarin 6, coumarin 6H, coumarin 7, coumarin 30, coumarin 47, coumarin 102, coumarin 106, coumarin 120, coumarin 151, coumarin 152, coumarin 152A, coumarin 153, coumarin 311, coumarin 307, coumarin 314, coumarin 334, coumarin 337, coumarin 343, coumarin 440, coumarin 450, coumarin 456, coumarin 460, coumarin 461, coumarin 466, coumarin 478, coumarin 480, coumarin 481, coumarin 485, coumarin 490, coumarin 500, coumarin 503, coumarin 504, coumarin 510, coumarin 515, coumarin 519, coumarin 521, coumarin 522, coumarin 523, coumarin 535, coumarin 540, coumarin 540A, coumarin 548, 5-ethylamino-9-diethylaminobenzo[a]phenoxazinium (EtNBA), 5-ethyl-amino-9-diethylaminobenzo[a]phenothiazinium (EtNBS), 5-ethylamino-9-diethylaminobenzo[a]pheno-selenazinium (EtNBSe), chlorpromazine, chlorpromazine derivatives, chlorophyll derivatives, bacterio-chlorophyll derivatives, metal-ligand complexes, tris(2,2'-bipyridine)ruthenium (II) dichloride (RuBPY), tris(2,2'-bipyridine)rhodium (II) dichloride (RhBPY), tris(2,2'-bipyridine)platinum (II) dichloride (PtBPY), pheophorbide a, merocyanine 540, vitamin D, 5-amino-laevulinic acid, photosan, chlorin e6, chlorin e6 ethylenediamide, mono-L-aspartyl chlorin e6, phenoxazine Nile blue derivatives, stilbene, stilbene derivatives, and 4(N-(2-hydroxyethyl)-N-methyl)-aminophenyl)-4'-(6-hydroxyhexylsulfonyl)stilbene (APSS).

10. The method of claim 8 wherein the at least one photo-active molecular agent includes at least one biogenic photo-active molecular agent that is specific to a particular substance within the particular volume of material.

11. The method of claim 10 wherein the at least one biogenic photo-active molecular agent includes a segment selected from the group consisting of DNA, RNA, amino acids, proteins, antibodies, ligands, haptens, carbohydrate receptors or complexing agents, lipid receptors or complexing agents, protein receptors or complexing agents, chelators, and encapsulating vehicles.

12. The method of claim 11 wherein the at least one biogenic photo-active molecular agent further includes a segment which is photo-activated when subject to light sufficient to promote a simultaneous two-photon excitation.

13. A method for producing at least one photo-activated molecular agent in a particular volume of a material, the method comprising treating the particular volume of the material with light sufficient to promote optical excitation of at least one photo-active molecular agent contained in the particular volume of the material, wherein the at least one photo-active molecular agent becomes a photo-activated molecular agent in the particular volume of the material.

14. The method of claim 13 wherein the at least one photo-active molecular agent includes at least one biogenic photo-active molecular agent that is specific to a particular substance within the particular volume of material.

15. The method of claim 14 wherein the at least one biogenic photo-active molecular agent includes a segment selected from the group consisting of DNA, RNA, amino acids, proteins, antibodies, ligands, haptens, carbohydrate receptors or complexing agents, lipid receptors or complexing agents, protein receptors or complexing agents, chelators, and encapsulating vehicles.

16. The method of claim 15 wherein the at least one biogenic photo-active molecular agent further includes a segment which is photo-activated when subject to light sufficient to promote optical excitation.

17. A method for producing at least one photo-activated therapeutic agent in a particular volume of a material, the method comprising directing near infra-red light to specific regions of interest within the material, including regions substantially below a material surface, said light being selected to penetrate the material and to promote two photon excitation (TPE) substantially only at a confocal zone; controlling the location of said confocal zone over a range of depths within said material; and using TPE, photo-activating at least one of said at least one therapeutic agent over said range of depths within said material, thereby producing at least one photo-activated agent substantially only at the confocal zone.

18. The method of claim 17 wherein said directing step includes directing a laser light to said particular volume.

19. The method of claim 18 wherein said directing step includes directing a pulsed laser light to said particular volume.

20. The method of claim 19 wherein said laser is operated to produce sub-nanosecond duration pulses.

21. The method of claim 19 wherein said laser produces a pulse frequency above about 75 megahertz.

22. The method of claim 19 wherein said laser pulses have energies of about 20 nanojoules.

23. The method of claim 17 wherein said method causes simultaneous TPE at said confocal zone.

* * * * *